United States Patent
Katsuta et al.

(10) Patent No.: US 9,974,732 B2
(45) Date of Patent: May 22, 2018

(54) CLEANSING COMPOSITION

(71) Applicant: KAO CORPORATION, Tokyo (JP)

(72) Inventors: Izumi Katsuta, Bunkyo-ku (JP); Kouji Endou, Katsushika-ku (JP); Mayuko Hirahara, Bunkyo-ku (JP); Satoshi Ozawa, Wakayama (JP); Eiko Nishisaka, Osaka (JP); Tetsuji Kitou, Iwade (JP)

(73) Assignee: KAO CORPORATION, Tokyo (JP)

( * ) Notice: Subject to any disclaimer, the term of this patent is extended or adjusted under 35 U.S.C. 154(b) by 0 days. days.

(21) Appl. No.: 14/917,513

(22) PCT Filed: Jul. 11, 2014

(86) PCT No.: PCT/JP2014/068538
§ 371 (c)(1),
(2) Date: Mar. 8, 2016

(87) PCT Pub. No.: WO2015/059961
PCT Pub. Date: Apr. 30, 2015

(65) Prior Publication Data
US 2016/0213594 A1      Jul. 28, 2016

(30) Foreign Application Priority Data

Oct. 24, 2013  (JP) ................................ 2013-221565

(51) Int. Cl.
| | |
|---|---|
| C11D 1/02 | (2006.01) |
| C11D 1/29 | (2006.01) |
| A61K 8/36 | (2006.01) |
| A61K 8/44 | (2006.01) |
| A61K 8/46 | (2006.01) |
| A61K 8/81 | (2006.01) |
| A61Q 19/10 | (2006.01) |

(Continued)

(52) U.S. Cl.
CPC ............ *A61K 8/8158* (2013.01); *A61K 8/361* (2013.01); *A61K 8/44* (2013.01); *A61K 8/463* (2013.01); *A61K 8/466* (2013.01); *A61K 8/604* (2013.01); *A61Q 19/10* (2013.01); *C11D 1/37* (2013.01); *C11D 3/3719* (2013.01); *C11D 1/06* (2013.01); *C11D 1/14* (2013.01); *C11D 1/143* (2013.01); *C11D 1/146* (2013.01); *C11D 1/29* (2013.01)

(58) Field of Classification Search
CPC ........... C11D 1/02; C11D 1/29; C11D 1/3719; C11D 3/3769; A61K 8/36; A61K 8/44; A61K 8/46; A61K 8/81; A61Q 19/10
See application file for complete search history.

(56) References Cited

U.S. PATENT DOCUMENTS 5,019,377 A *   5/1991   Torgerson ............ A61K 8/8158
                                                                424/47
5,221,530 A     6/1993   Janchitraponvej et al.
(Continued)

FOREIGN PATENT DOCUMENTS

JP        2-1713 A        1/1990
JP     2001-513538 A      9/2001
(Continued)

OTHER PUBLICATIONS

International Search Report dated Sep. 16, 2014 in PCT/JP14/068538 filed Jul. 11, 2014.

*Primary Examiner* — Brian P Mruk
(74) *Attorney, Agent, or Firm* — Oblon, McClelland, Maier & Neustadt, L.L.P.

(57) ABSTRACT

Cleansing composition comprising the following components (A), (B), and (C):
(A) 0.02% by mass or larger and 10% by mass or smaller of a polymer comprising 85 to 100% by mass as constitutional units of
a1: a constitutional unit represented by the formula (1):

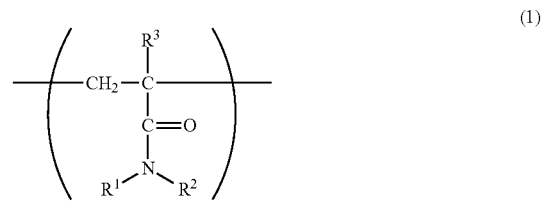

(1)

wherein $R^1$ and $R^2$ each represents an alkyl group having 1 to 4 carbon atoms and optionally having a hydroxy group, or a hydrogen atom, and $R^3$ represents a hydrogen atom or a methyl group, and
a2: a constitutional unit represented by the formula (2):

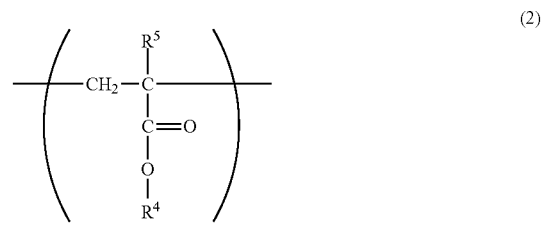

(2)

wherein $R^4$ represents a linear or branched alkyl group having 1 to 22 carbon atoms, and $R^5$ represents a hydrogen atom or a methyl group;
(B) 0.5% by mass or larger and 40% by mass or smaller of an anionic surfactant; and
(C) water.

13 Claims, No Drawings

(51) Int. Cl.
    *C11D 3/37*     (2006.01)
    *C11D 1/37*     (2006.01)
    *A61K 8/60*     (2006.01)
    *C11D 1/06*     (2006.01)
    *C11D 1/14*     (2006.01)

(56) References Cited

U.S. PATENT DOCUMENTS

| | | |
|---|---|---|
| 2007/0116660 A1 | 5/2007 | Kim et al. |
| 2008/0261845 A1 | 10/2008 | Yamamoto et al. |

FOREIGN PATENT DOCUMENTS

| | | |
|---|---|---|
| JP | 2001-513539 A | 9/2001 |
| JP | 2007-514031 A | 5/2007 |
| JP | 2008-285479 A | 11/2008 |
| JP | 2008-285480 A | 11/2008 |
| JP | 209-263289 | 11/2009 |
| JP | 2009-263290 A | 11/2009 |
| JP | 2011-225467 | 11/2011 |
| JP | 2014-136724 A | 7/2014 |
| JP | 2015-81341 A | 4/2015 |
| JP | 2015-81342 A | 4/2015 |
| JP | 2015-108112 A | 6/2015 |
| JP | 2015-124196 A | 7/2015 |
| WO | 99/09947 A1 | 3/1999 |
| WO | 99/09948 A1 | 3/1999 |

\* cited by examiner

CLEANSING COMPOSITION

FIELD OF THE INVENTION

The present invention relates to a cleansing composition.

BACKGROUND OF THE INVENTION

Among performances required for skin cleansing agents to clean the face or the whole body, a feel with frictional resistance (stop feeling) which indicates the complete washing off of a cleansing agent as a feel upon rinsing is important as well as favorable foaming upon cleansing. Preferred skin cleansing agents require a shorter time until this stop feeling is perceived in the process of rinsing, and can offer refreshed feeling as the skin feel after cleansing.

Heretofore, a large number of skin cleansing compositions containing a general-purpose surfactant polyoxyethylene alkyl ether sulfate as a main component have been disclosed in this field, and techniques of controlling a feel upon rinsing or skin feel after cleansing have been studied. Patent Publications 1 and 2 state that in personal cleansing compositions containing a water-soluble surfactant such as polyoxyethylene alkyl ether sulfate as a main component, the addition of water-insoluble oil such as polyisobutene or silicone oil offers an improved rinse feel upon rinsing.

Patent Publications 3 and 4 describe cleansing compositions containing a particular surfactant and a cationic polymer. These state that the cleansing compositions were improved in terms of stop feeling upon rinsing when used for skin cleansing.

PATENT PUBLICATION (Patent Publication 1) JP-A 2001-513539
(Patent Publication 2) JP-A 2001-513538
(Patent Publication 3) JP-A 2008-285479
(Patent Publication 4) JP-A 2008-285480

SUMMARY OF THE INVENTION

The present invention relates to a cleansing composition comprising the following components (A), (B), and (C):

(A) 0.02% by mass or larger and 10% by mass or smaller of a polymer comprising 85 to 100% by mass of a1 and a2 as constitutional units:

a1: a constitutional unit represented by the formula (1):

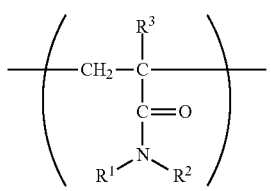

wherein $R^1$ and $R^2$ are the same or different and each represents an alkyl group having 1 to 4 carbon atoms and optionally having a hydroxy group, or a hydrogen atom, and $R^3$ represents a hydrogen atom or a methyl group, and a2: a constitutional unit represented by the formula (2):

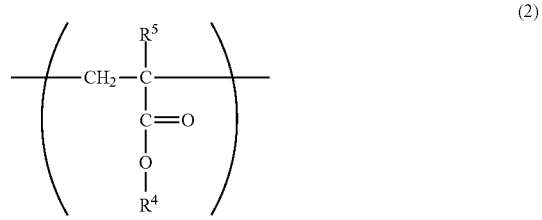

wherein $R^4$ represents a linear or branched alkyl group having 1 to 22 carbon atoms, and $R^5$ represents a hydrogen atom or a methyl group;

(B) 0.5% by mass or larger and 40% by mass or smaller of an anionic surfactant selected from b1, b2, and b3:

b1: the formula (3):

$$R^6\text{-D-OSO}_3X^1 \quad (3)$$

wherein $R^6$ represents a linear or branched alkyl group or alkenyl group having 10 to 22 carbon atoms, D represents $-(OCH_2CH_2)_n-$, in which n represents a number of 0 to 10, and $X^1$ represents an alkali metal, an alkaline earth metal, an ammonium, or an organic base, b2: the formula (4):

$$R^7\text{-E-SOX}^2 \quad (4)$$

wherein $R^7$ represents an optionally substituted linear or branched alkyl group or alkenyl group having 10 to 22 carbon atoms, E represents $-(OCH_2CH_2)_m-$ or $-CO-O-C_2H_4-$, in which m represents a number of 0 to 10, and $X^2$ represents an alkali metal, an alkaline earth metal, an ammonium, or an organic base, and b3: the formula (5):

$$R^8\text{-G-COOX}^3 \quad (5)$$

wherein $R^8$ represents a linear or branched alkyl group or alkenyl group having 10 to 22 carbon atoms, G represents $-(OCH_2CH_2)_p-OCH_2-$ or $-CO-NH-CR^9H-$, in which p represents a number of 0 to 10, and $R^9$ represents a hydrogen atom or a methyl group, and $X^3$ represents an alkali metal, an alkaline earth metal, an ammonium, or an organic base; and (C) water.

DETAILED DESCRIPTION OF THE INVENTION

The addition of an oil component to a skin cleansing composition as described in Patent Publications 1 and 2, particularly, when the skin cleansing composition is used for cleansing the whole body, presents problems such as insufficient stop feeling upon rinsing and stickiness without a refreshed feel due to strong feeling of residues on the skin or strong oily feeling after washing off.

The cleansing compositions of Patent Publications 3 and 4 may cause perceivable stickiness as the skin feel after towel-drying following rinsing and are thus required to be further improved, though they produce high stop feeling upon rinsing The present invention relates to a cleansing composition which is excellent in foamability and foam quality and produces favorable stop feeling upon rinsing and a refreshed feel after towel-drying.

The present inventors found that a cleansing composition which can overcome the problems mentioned above can be obtained by the combined use of a particular polymer and a particular anionic surfactant.

The cleansing composition of the present invention foams quickly upon cleansing, is excellent in foam quality with a sufficient foam volume, is free from feeling of residues on the skin at the completion of rinsing, and offers a favorable stop feeling. In addition, the cleansing composition of the present invention can produce a non-sticky dry feel because of only a small amount of residues on the skin immediately after towel-drying following cleansing and produce natural bare skin feeling without feeling of residues on the skin after drying.

The component (A) used in the present invention is a polymer comprising a1 and a2 as constitutional units.

a1 is a constitutional unit represented by the formula (1) and is derived from a monomer represented by the formula (1'):

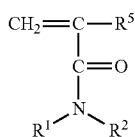

(1')

wherein $R^1$, $R^2$, and $R^3$ are as defined above.

Preferably, $R^1$ and $R^2$ are each independently a hydrogen atom, a methyl group, an ethyl group, or a t-butyl group. More preferably, each of $R^1$ and $R^2$ is a methyl group from the viewpoint of water solubility and safety.

Examples of the monomer represented by the formula (1') include acrylamide, N-methylacrylamide, N-ethylacrylamide, N-t-butylacrylamide, N,N-dimethylacrylamide, N,N-diethylacrylamide, N-2-hydroxyethylacrylamide, N-methylmethacrylamide, and N-ethylmethacrylamide. At least one or more in combination selected from these monomers can be used.

Among them, N,N-dimethylacrylamide, N,N-diethylacrylamide, N-2-hydroxyethylacrylamide, and N-t-butylacrylamide is preferred, N,N-dimethylacrylamide, N,N-2-hydroxyethylacrylamide, and N-t-butylacrylamide is more preferred, and N,N-dimethylacrylamide is further preferred, from the viewpoint of solubility in water and a feel upon application.

a2 is a constitutional unit represented by the formula (2) and is derived from a monomer represented by the formula (2'):

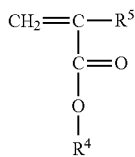

(2')

wherein $R^4$ and $R^5$ are as defined above.

$R^4$ is preferably a linear or branched alkyl group having 1 to 22 carbon atoms, more preferably a linear or branched alkyl group having 4 to 18 carbon atoms, from the viewpoint of foam volume upon cleansing and skin feel upon rinsing.

Examples of the monomer represented by the formula (2') include methyl methacrylate, ethyl methacrylate, butyl methacrylate, t-butyl methacrylate, 2-ethylhexyl methacrylate, lauryl methacrylate, stearyl methacrylate, behenyl methacrylate, methyl acrylate, ethyl acrylate, butyl acrylate, t-butyl acrylate, 2-ethylhexyl acrylate, lauryl acrylate, stearyl acrylate, and behenyl acrylate. At least one or more in combination selected from these monomers can be used.

Among them, butyl methacrylate, t-butyl methacrylate, lauryl methacrylate, stearyl methacrylate, and butyl acrylate is preferred from the viewpoint of reduced solubility in water upon application and a non-sticky dry feel. Lauryl methacrylate is more preferred from the viewpoint of producing smooth and moist feeling of the skin without powdery texture on the skin after drying.

In the component (A), the mass ratio between a1 and a2, (a1/a2) is preferably 5/95 to 95/5, more preferably 20/80 to 80/20, further preferably 40/60 to 80/20, from the viewpoint of the reduced water solubility of formulations and a non-sticky dry feel. This can suppress sliminess during rinsing and suppress excessive feeling of friction. The mass ratio between a1 and a2, a1/a2, can be determined by proton nuclear magnetic resonance (1H-NMR) measurement mentioned later.

The polymer as the component (A) is preferably composed of the constitutional units a1 and a2 and can contain other constitutional units without impairing the performance. The component (A) comprises 85 to 100% by mass of sum of the components a1 and a2 based on all constitutional units and comprises preferably 91% by mass or larger and 100% by mass or smaller, more preferably 95% by mass or larger and 100% by mass or smaller, further preferably 97% by mass or larger and 100% by mass or smaller, even further preferably 100% by mass, of sum of the components a1 and a2 based on all constitutional units. The component (A) comprising the constitutional units a1 and a2 at a higher concentration results in a cleansing composition excellent in feeling of foam thickness (which means that a user feels some distance between both hands when sandwiching foam between the hands).

Specific examples of monomers constituting the constitutional units other than the constitutional units a1 and a2 may include, but are not limited to, (meth)acrylic acid, N-vinylpyrrolidone, diacetoneacrylamide, vinyl alcohol, (meth)acrylic acid (poly)ethylene glycol ester, styrene, and alkene having 2 to 10 carbon atoms.

The component (A) is preferably a nonionic polymer from the viewpoint of conferring a feel upon rinsing.

In the polymer as the component (A), the constitutional units a1 and a2 may be random-copolymerized or block-copolymerized, and are preferably random-copolymerized.

The method for producing the polymer as the component (A) is not limited. The polymer as the component (A) can be obtained, for example, by the addition polymerization (e.g., radical polymerization or ionic polymerization) of a1 and a2, and optionally other components using a general polymerization method such as a solution polymerization method, a suspension polymerization method, an emulsion polymerization method, or a dispersion polymerization method. Radical polymerization is preferred from the viewpoint of ease of synthesis and the flexibility in formulation.

A general radical polymerization initiator can be used as a radical polymerization initiator for the polymerization. Examples thereof include: peroxide initiators such as lauroyl peroxide, benzoyl peroxide, and ammonium persulfate; and azo initiators such as 2,2'-azobis(2,4-dimethylvaleronitrile), 2,2'-azobisisobutyronitrile, and dimethyl 2,2'-azobis(isobutyrate). The preferred amount of the radical polymerization initiator used varies depending on the types and concentrations of monomers, the type of the initiator, reaction temperature, etc. Usually, the amount of the radical polymerization initiator used is preferably 0.01 to 10% by mol, more preferably 0.1 to 8% by mol, with respect to the total amount of monomers used in production.

An organic solvent, such as a lower alcohol (ethanol, isopropanol, etc.), a ketone (acetone or methyl ethyl ketone), or ethyl acetate, which is capable of dissolving both the starting material monomers and the polymer to be produced can be used as a polymerization solvent.

The polymer as the component (A) can be produced by a general method such as a method which involves adding monomers and a polymerization initiator together with a solvent, etc., into a reaction vessel, if necessary removing dissolved oxygen in the system by, for example, substitution by an inert gas such as nitrogen, then heating the contents to 30 to 120° C., followed by polymerization for approximately 1 to 20 hours. The conversion rate of each monomer after the completion of the polymerization is preferably 90 to 100% by mol, more preferably 95 to 100% by mol, further preferably 99 to 100% by mol, from the viewpoint of producing a polymer having a compositional ratio according to the ratio of the added monomers. The monomer conversion rate mentioned above can be measured by liquid chromatography. Specific conditions therefor are described in Examples.

The polymer obtained by the polymerization can be purified, for example, through the removal of unreacted monomers, by known methods such as further addition of the initiator, reprecipitation, or membrane purification. Alternatively, a solution containing the polymer after the polymerization may be mixed directly into the cleansing composition without being purified or may be mixed into the cleansing composition after replacement of the solvent used in the polymerization with a different solvent. The solvent replacement can be easily carried out by the addition of the different solvent after distilling off by heating under reduced pressure.

The weight-average molecular weight of the component (A) is preferably 10,000 or larger, more preferably 40,000 or larger, further preferably 50,000 or larger and is preferably 500,000 or smaller, more preferably 350,000 or smaller, further preferably 200,000 or smaller, even further preferably 100,000 or smaller, from the viewpoint of foamability upon cleansing and the control of preparation viscosity. The weight-average molecular weight of the component (A) is preferably 10,000 to 500,000, more preferably 40,000 to 350,000, further preferably 50,000 to 200,000, even further preferably 50,000 to 100,000.

The weight-average molecular weight of the component (A) is measured by a method mentioned later.

Also preferably, the component (A) has low solubility in water. For example, the solubility of the component (A) in water is defined as follows: X g of the polymer is mixed with 100 g of water at 20° C., and when the total amount of the polymer is thoroughly dissolved (the solution is clear as a whole without insoluble matter), the maximum amount of the polymer is defined as a degree of solubility=X g/100 g. In this case, the degree of solubility of the component (A) is preferably 1 g or lower, more preferably 0.5 g or lower, further preferably 0.1 g or lower, with respect to 100 g of water at 20° C. and is even further preferably undissolved. The component (A) having such a low degree of solubility in water can improve foam quality through its combination with the component (B) mentioned later. This can suppress the sliminess of an anionic surfactant upon rinsing and substantially minimize feeling of residues from a salt or a complex of the surfactant on the skin at the completion of rinsing. The resulting cleansing composition, unlike conventional cleansing agents, can offer a natural skin feel (which means that a user feels as if he or she had washed the skin with water alone).

The content of the component (A) in the whole composition is 0.02% by mass or larger, preferably 0.1% by mass or larger, more preferably 0.25% by mass or larger, further preferably 0.4% by mass or larger and is 10% by mass or smaller, preferably 4% by mass or smaller, more preferably 2% by mass or smaller, further preferably 1% by mass or smaller, from the viewpoint of the skin feel upon rinsing and solubility or dispersibility in a preparation. The content of the component (A) in the whole composition is 0.02 to 10% by mass, preferably 0.1 to 4% by mass, more preferably 0.25 to 2% by mass, further preferably 0.4 to 1% by mass.

The component (B) is an anionic surfactant selected from the group consisting of b1, b2, and b3 represented by the formulas (3), (4), and (5), respectively.

Specific examples of the anionic surfactant represented by b1 include alkyl sulfate having a linear or branched alkyl group having 10 to 22 carbon atoms and alkyl ether sulfate having a linear or branched alkyl group having 10 to 22 carbon atoms.

Specific examples of the anionic surfactant represented by b2 include sulfonate having a linear or branched alkyl group having 10 to 22 carbon atoms, alkenyl sulfonate having a linear or branched alkenyl group having 10 to 22 carbon atoms such as α-olefin sulfonate (AOS) having a linear or branched alkenyl group having 10 to 22 carbon atoms, and linear or branched fatty acid ester sulfonate having 10 to 22 carbon atoms.

Specific examples of the anionic surfactant represented by b3 include alkyl ether carboxylate having a linear or branched alkyl group having 10 to 22 carbon atoms and linear or branched fatty acid acyl amino acid salt having 10 to 22 carbon atoms.

In the formulas (3), (4), and (5), none of $R^6$, $R^7$, and $R^8$ contains benzene rings.

Among them, alkyl sulfate having a linear alkyl group having 10 to 22 carbon atoms, alkyl ether sulfate containing ethylene glycol added to a linear alkyl group having 10 to 22 carbon atoms, α-olefin sulfonate having a linear or branched alkenyl group having 10 to 22 carbon atoms, alkyl ether carboxylate having a linear alkyl group having 10 to 22 carbon atoms, and N-lauric acid acyl L-alanine salt is preferred, and alkyl ether sulfate is more preferred, from the viewpoint of foamability and cleansing performance. The alkyl ether sulfate preferably has an alkyl group having 12 to 14 carbon atoms. The average number of moles of ethylene oxide added is preferably 0.5 to 5, more preferably 1 to 4.

In the component (B), $X^1$, $X^2$, and $X^3$ in the formulas (3), (4), and (5) each represents an alkali metal such as sodium or potassium; an alkaline earth metal such as calcium or magnesium; an ammonium; an alkanolamine such as monoethanolamine, diethanolamine, or triethanolamine; or a basic amino acid such as arginine or lysine, and form a salt of an alkali metal such as sodium or potassium; a salt of an alkaline earth metal such as calcium or magnesium; an ammonium salt; a salt of an alkanolamine such as monoethanolamine, diethanolamine, or triethanolamine; or a salt of a basic amino acid such as arginine or lysine, in the anionic surfactants represented by b1 to b3. Among them, an alkali metal salt or an ammonium salt is preferred from the viewpoint of solubility and stability.

One or more components (B) can be used. The content of the component (B) as a salt in the whole composition may be 0.5% by mass or larger, preferably 2% by mass or larger, more preferably 5% by mass or larger and may be 40% by mass or smaller, preferably 20% by mass or smaller, more preferably 15% by mass or smaller, from the viewpoint of the solubility or dispersibility of the component (A), foam quality upon cleansing, and the skin feel. The content of component (B) as a salt in the whole composition is 0.5 to 40% by mass, preferably 2 to 20% by mass, more preferably 5 to 15% by mass.

The cleansing composition of the present invention is preferably a cleansing composition comprising b1 represented by the formula (3) and/or b2 represented by the formula (4), and also b3 represented by the formula (5) as the component (B), more preferably a cleansing composition comprising b1 represented by the formula (3) and b3 represented by the formula (5) as the component (B), from the viewpoint of the absence of sliminess at the initial stage of rinsing, feeling of foam thickness upon cleansing, and foaming quickness.

The mass ratio between the sum of b1 and b2, and b3, ((b1+b2)/(b3)) is preferably 0.085 to 3, more preferably 0.1 to 2, further preferably 0.2 to 1.5, from the viewpoint of the absence of sliminess at the initial stage of rinsing and the foam thickness.

The mass ratio between the sum of b1 and b2, and b3, ((b1+b2)/(b3)) is preferably 0.25 to 12, more preferably 0.3 to 11, further preferably 0.5 to 10, from the viewpoint of foaming.

The mass ratio between the sum of b1 and b2, and b3, ((b1+b2)/(b3)) is preferably 0.1 to 9, more preferably 0.14 to 7, further preferably 0.2 to 5, from the viewpoint of further improvements in the absence of sliminess at the initial stage of rinsing, feeling of foam thickness upon cleansing, and foaming quickness.

The cleansing composition of the present invention in which these components b1 and/or b2 and b3 are used in combination foams quickly, permits pleasant cleansing with excellent foam thickness upon cleansing, and produces cleansing feeling with refreshed feeling because of low sliminess at the initial stage of rinsing. The cleansing composition of the present invention is therefore suitable for the cleansing of body parts including face, limbs, and trunk.

In the cleansing composition of the present invention, the mass ratio between the components (A) and (B), (A)/(B) is preferably 0.0025 or higher, more preferably 0.005 or higher, further preferably 0.02 or higher, even further preferably 0.035 or higher and is preferably 8 or lower, more preferably 1 or lower, further preferably 0.2 or lower, from the viewpoint that: the component (A) can be dissolved or dispersed in the composition; sliminess upon rinsing can be suppressed; a moderate stop feeling can be conferred; bare skin feeling as if the skin had been washed with water is offered to the skin after towel-drying; stickiness at the moment of drying can be suppressed. The mass ratio between the components (A) and (B), (A)/(B) is preferably 0.0025 to 8, more preferably 0.005 to 1, further preferably 0.02 to 1, even further preferably 0.035 to 0.2.

In the present invention, the content of water as the component (C) forms a balance among the components in relation to use as a solvent in the composition. The content of water as the component (C) in the whole composition is preferably 35% by mass or larger, more preferably 50% by mass or larger and is preferably 99% by mass or smaller, preferably 98% by mass or smaller, preferably 96% by mass or smaller, preferably 94% by mass or smaller, more preferably 90% by mass or smaller, further preferably 80% by mass or smaller. The content of the component (C) in the whole composition is preferably 35 to 99% by mass, more preferably 50 to 90% by mass, further preferably 50 to 80% by mass.

The component (A) has low solubility in water, as mentioned above. Specific performance was found by mixing the components (A) and (B) to dissolve or disperse the component (A) therein. Specifically, higher foam quality than ever. More specifically, the resulting foam has high elasticity and can have foam quality so as to prevent both hands from being stuck to each other when the foam is sandwiched between the hands. Moreover, the sliminess of the anionic surfactant upon rinsing can be suppressed. At the completion of rinsing, a salt (e.g., scum) or a complex of the surfactant is less adsorbed on the skin so that residues are hardly felt on the skin. The resulting cleansing composition can offer a feel different from that of conventional cleansing agents, specifically, a more natural skin feel (the natural skin feel means that a user feels as if he or she had washed the skin with water alone).

The cleansing composition of the present invention may further comprise an amphoteric surfactant as a component (D) and can thereby produce higher foam quality.

The amphoteric surfactant as the component (D) can be any amphoteric surfactant for use in ordinary cleansing compositions. Examples thereof include: acetic acid betaine-type surfactants such as lauryl dimethylaminoacetic acid betaine; amine oxide-type surfactants such as lauryl dimethylamine oxide; imidazolinium betaine-type surfactants such as 2-alkyl-N-carboxymethyl-N-hydroxyethylimidazolinium betaine; amide betaine-type surfactants such as lauramidopropyl betaine; and sulfobetaine-type surfactants such as lauryl hydroxy sulfobetaine.

Among them, an amide betaine-type surfactant such as lauramidopropyl betaine and/or a sulfobetaine-type surfactant such as lauryl hydroxy sulfobetaine is preferred from the viewpoint of foamability, a feel, and stability.

One or more components (D) can be used. The content of the component (D) in the whole composition is preferably 0.5% by mass or larger, more preferably 1% by mass or larger, further preferably 1.5% by mass or larger, even further preferably 2% by mass or larger, far further preferably 3% by mass or larger and is preferably 30% by mass or smaller, more preferably 15% by mass or smaller, further preferably 10% by mass or smaller, from the viewpoint of improving foam quality, achieving fine foam, and further imparting high elasticity to foam or from the viewpoint of conferring foam quality with transparency. The content of the component (D) in the whole composition is preferably 0.5 to 30% by mass, more preferably 1.5 to 15% by mass, further preferably 3 to 10% by mass.

The cleansing composition of the present invention may further comprise a nonionic surfactant having HLB of 11 or higher as a component (E) and can thereby improve foamability and foam volume. The nonionic surfactant as the component (E) has HLB of 11 or higher and preferably has HLB of 15 to 17.

In this context, HLB refers to an index which indicates a hydrophilic-lipophilic balance. In the present invention, a value calculated using the following expression of Oda, Teramura, etc. is used:

$$HLB = \frac{\Sigma \text{ Inorganic value}}{\Sigma \text{ Organic value}} \times 10$$

The nonionic surfactant as the component (E) can be any nonionic surfactant for use in ordinary cleansing compositions. Examples thereof include polyglycerin fatty acid ester, polyethylene glycol fatty acid ester, polyoxyethylene glycerin fatty acid ester, propylene glycol fatty acid ester, polyoxyethylene polyoxypropylene glycol, sorbitan fatty acid ester, polyoxyethylene sorbitan fatty acid ester, polyoxyethylene sorbit fatty acid ester, polyoxyethylene castor oil, polyoxyethylene hydrogenated castor oil, polyoxyethylene hydrogenated castor oil fatty acid ester, polyalkyl glyceryl ether, polyoxyethylene alkyl ether, polyoxyethylene alkyl ether fatty acid ester, sucrose fatty acid ester, alkyl polyglucoside, and alkyl glyceryl ether.

Among them, polyoxyethylene sorbitan fatty acid ester and/or alkyl polyglucoside is preferred from the viewpoint of foamability, feel, and stability.

One or more components (E) can be used. The content of the component (E) in the whole composition is preferably 0.5% by mass or larger, more preferably 1% by mass or larger, further preferably 1.5% by mass or larger, even further preferably 3% by mass or larger and is preferably 30% by mass or smaller, more preferably 15% by mass or smaller, further preferably 10% by mass or smaller, from the viewpoint of foaming quickness upon cleansing and the skin feel. The content of the component (E) in the whole composition is preferably 0.5 to 30% by mass, more preferably 1.5 to 15% by mass, further preferably 3 to 10% by mass.

The cleansing composition of the present invention may further comprise a water-soluble polyvalent metal salt as a component (F) and can thereby produce an excellent strength in stop feeling at the completion of rinsing and refreshed feeling upon application.

Examples of the water-soluble polyvalent metal salt as the component (F) include inorganic salts of aluminum or an alkaline earth metal such as magnesium, or calcium with halogen or an inorganic acid such as, sulfuric acid, sulfonic acid, sulfurous acid, or phosphoric acid and organic salts of aluminum or the alkaline earth metal with an organic acid such as lactic acid, acetic acid, or malic acid. Examples thereof include one or more water-soluble aluminum salts selected from the group consisting of potassium aluminum sulfate (alum), ammonium aluminum sulfate, aluminum chloride, aluminum sulfate, aluminum lactate, and the like, and one or more alkaline earth metal salts selected from the group consisting of magnesium sulfate, magnesium chloride, calcium chloride, and the like.

Among them, a water-soluble aluminum salt is preferred, and potassium aluminum sulfate is more preferred, from the viewpoint of excellent stop feeling at the completion of rinsing when the components (A) and (B) are combined for cleansing.

One or more water-soluble polyvalent metal salts can be used as the component (F). The content of the component (F) in the whole composition is preferably 0.01 to 5% by mass, more preferably 0.05 to 3% by mass, further preferably 0.1 to 1% by mass, from the viewpoint of rinsability.

In the present invention, the mass ratio between the component (B) and the component (F), (B)/(F) is preferably 1 to 200, more preferably 5 to 100, further preferably 8 to 60, from the viewpoint of excellent stop feeling at the completion of rinsing.

The mass ratio between the component (A) and the component (F), (A)/(F) is preferably 0.5 to 20, more preferably 1 to 10, further preferably 1.2 to 9, from the viewpoint of excellence in feeling no residues on the skin at the completion of rinsing.

The cleansing composition of the present invention may further contain, if necessary, various components for use in ordinary cleansing compositions. The cleansing composition of the present invention can appropriately contain, for example, moisturizers such as propylene glycol, dipropylene glycol, glycerin, and sorbitol; viscosity adjusters such as methylcellulose and polyoxyethylene glycol distearate; bactericides such as triclosan, triclocarban, and isopropylmethylphenol; anti-inflammatory agents such as potassium glycyrrhizinate and tocopherol acetate; antiseptics such as methylparaben, butylparaben, phenoxyethanol, and benzoate; chelating agents such as a potassium salt or a sodium salt of ethylenediaminetetraacetic acid (EDTA), cyclohexanediaminetetraacetic acid (CDTA), citric acid, or polyphosphoric acid; and other components such as dyes, fragrances, ultraviolet absorbers, antioxidants, and pearling agents.

The cleansing composition of the present invention can be produced by an ordinary method which involves weighing the components to be formulated and mixing the components in an arbitrary order into water or an aqueous medium composed mainly of water containing an additional water-soluble solvent such as an alcohol. The cleansing composition thus produced can be applied to, for example, a skin cleansing agent such as a body shampoo, a face wash, hand soap, or a cleanser.

Also, the composition of the present invention comprising the components (A), (B), and (C) can be used as a skin cleansing agent.

The method for using the cleansing composition of the present invention involves, for example, putting the cleansing composition on a palm, or in some cases, on a towel or a cleansing sponge, diluting the composition with water, foaming it, thoroughly spreading the foam over the body, rubbing the body with the foam, and washing off the foam with water.

The cleansing composition of the present invention has a pH of preferably 4.5 to 11, more preferably 5.5 to 9, when diluted 20-fold with ion-exchanged water at 25° C. Adjusting the pH within this range is preferred, because of favorable foamability, foam volume and foam quality upon cleansing and because of low irritation on the skin.

The pH of the cleansing composition can be adjusted, if necessary, with a pH adjuster, for example, an inorganic acid such as hydrochloric acid, sulfuric acid, or phosphoric acid; an organic acid such as citric acid, succinic acid, lactic acid, malic acid, pyrrolidonecarboxylic acid, tartaric acid, glycolic acid, or ascorbic acid; an acidic amino acid such as glutamic acid or aspartic acid; a hydroxide such as sodium hydroxide or potassium hydroxide; ammonia or ammonia water; or a basic amino acid such as arginine or lysine.

The cleansing composition of the present invention can be produced, for example, by the following method.

The component (B) and the component (C) are mixed and the mixture is heated to 60° C. or higher, preferably 70° C. or higher. The component (D) and the component (E) are further added thereto, if necessary, and a homogeneous mixture is obtained. An appropriate amount of a base component such as sodium hydroxide or an acid component such as malic acid is added thereto as a pH adjuster to adjust the pH of a 20-fold dilution within the desired range. To this solution, are added the component (A) and other polymers, and other components, and the mixture is further stirred to prepare a homogeneous mixture. The mixture can be cooled to 30° C. to obtain a cleansing composition.

The cleansing composition of the present invention is preferably in a liquid state from the viewpoint of foaming performance. Its viscosity at 25° C. is preferably 100 Pa·s or lower, more preferably 20 Pa·s or lower, further preferably 2 Pa·s or lower. In the present invention, the above viscosity may be measured using an oscillating viscometer (manufactured by A&D Co., Ltd., CVJ5000 model).

The cleansing composition of the present invention is suitable as a skin cleansing agent. In the case of use as a skin cleansing agent, the composition can cleanse the skin by applying the composition to the skin of the body, followed by rinsing.

In relation to the embodiments mentioned above, the present invention further discloses the following composition.

<1> A cleansing composition comprising the following components (A), (B), and (C):
(A) 0.02% by mass or larger and 10% by mass or smaller of a polymer comprising 85 to 100% by mass of a1 and a2 as constitutional units:
a1: a constitutional unit represented by the formula (1):

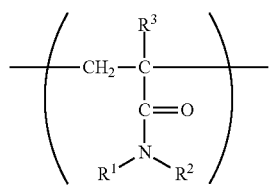

(1)

wherein $R^1$ and $R^2$ are the same or different and each represents an alkyl group having 1 to 4 carbon atoms and optionally having a hydroxy group, or a hydrogen atom, and $R^3$ represents a hydrogen atom or a methyl group, and
a2: a constitutional unit represented by the formula (2):

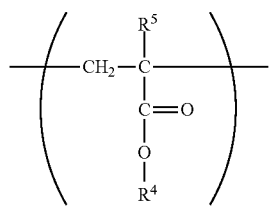

(2)

wherein $R^4$ represents a linear or branched alkyl group having 1 to 22 carbon atoms, and $R^5$ represents a hydrogen atom or a methyl group;
(B) 0.5% by mass or larger and 40% by mass or smaller of an anionic surfactant selected from the group consisting of b1, b2, and b3:

b1: the formula (3):

$$R^6\text{-D-OSO}_3X^1 \qquad (3)$$

wherein $R^5$ represents a linear or branched alkyl group or alkenyl group having 10 to 22 carbon atoms, D represents —(OCH$_2$CH$_2$)$_n$—, in which n represents a number of 0 to 10, and $X^1$ represents an alkali metal, an alkaline earth metal, an ammonium, or an organic base, b2: the formula (4):

$$R^7\text{-E-SO}_3X^2 \qquad (4)$$

wherein $R^7$ represents an optionally substituted linear or branched alkyl group or alkenyl group having 10 to 22 carbon atoms, E represents —(OCH$_2$CH$_2$)$_m$— or —CO—O—C$_2$H$_4$—, in which m represents a number of 0 to 10, and $X^2$ represents an alkali metal, an alkaline earth metal, an ammonium, or an organic base, and b3: the formula (5):

$$R^8\text{-G-COOX}^3 \qquad (5)$$

wherein $R^8$ represents a linear or branched alkyl group or alkenyl group having 10 to 22 carbon atoms, G represents —(OCH$_2$CH$_2$)$_p$—OCH$_2$— or —CO—NH—CR$^9$H—, in which p represents a number of 0 to 10, and $R^9$ represents a hydrogen atom or a methyl group, and $X^3$ represents an alkali metal, an alkaline earth metal, an ammonium, or an organic base; and
(C) water.

<2> The cleansing composition according to above <1>, wherein the weight-average molecular weight of the component (A) is preferably 10,000 to 500,000, more preferably 40,000 to 350,000, further preferably 50,000 to 200,000, even further preferably 50,000 to 100,000.

<3> The cleansing composition according to above <1> or <2>, wherein the mass ratio between a1 and a2, a1/a2 in the component (A) is preferably 5/95 to 95/5, more preferably 20/80 to 80/20, further preferably 40/60 to 80/20.

<4> The cleansing composition according to any one of above <1> to <3>, wherein the component (A) comprises preferably 91% by mass or larger and 100% by mass or smaller, more preferably 95% by mass or larger and 100% by mass or smaller, further preferably 97% by mass or larger and 100% by mass or smaller, even further preferably 100% by mass, of sum of the constitutional units a1 and a2 based on all constitutional units.

<5> The cleansing composition according to any one of above <1> to <4>, wherein a1 in the component (A) is preferably derived from a monomer selected from the group consisting of N,N-dimethylacrylamide, N,N-diethylacrylamide, N-2-hydroxyethylacrylamide, and N-t-butylacrylamide, more preferably derived from N,N-dimethylacrylamide.

<6> The cleansing composition according to any one of above <1> to <5>, wherein in the component (A) a2 is a constitutional unit represented by formula (2) and $R^4$ is a linear or branched alkyl group having 4 to 18 carbon atoms.

<7> The cleansing composition according to any one of above <1> to <6>, wherein the content of the component (A) in the whole composition is preferably 0.1% by mass or larger, more preferably 0.25% by mass or larger, further preferably 0.4% by mass or larger and is preferably 4% by mass or smaller, more preferably 2% by mass or smaller, further preferably 1% by mass or smaller.

<8> The cleansing composition according to any one of above <1> to <7>, wherein the component (B) is one or more selected from the group consisting of:
b1: alkyl sulfate having a linear or branched alkyl group having 10 to 22 carbon atoms and alkyl ether sulfate having a linear or branched alkyl group having 10 to 22 carbon atoms;
b2: sulfonate having a linear or branched alkyl group having 10 to 22 carbon atoms, alkenyl sulfonate having a linear or branched alkenyl group having 10 to 22 carbon atoms, and linear or branched fatty acid ester sulfonate having 10 to 22 carbon atoms; and
b3: alkyl ether carboxylate having a linear or branched alkyl group having 10 to 22 carbon atoms and linear or branched fatty acid acyl amino acid salt having 10 to 22 carbon atoms.

<9> The cleansing composition according to any one of above <1> to <8>, wherein the component (B) preferably comprises b1 represented by the formula (3) and/or b2 represented by the formula (4), and b3 represented by the formula (5), more preferably comprises b1 represented by the formula (3) and b3 represented by the formula (5).

<10> The cleansing composition according to any one of above <1> to <9>, wherein the mass ratio between the sum of b1 and b2, and b3, ((b1+b2)/(b3)) is preferably 0.085 to 3, more preferably 0.1 to 2, further preferably 0.2 to 1.5.

<11> The cleansing composition according to any one of above <1> to <9>, wherein the mass ratio between the sum of b1 and b2, and b3, ((b1+b2)/(b3)) is preferably 0.25 to 12, more preferably 0.3 to 11, further preferably 0.5 to 10.

<12> The cleansing composition according to any one of above <1> to <9>, wherein the mass ratio between the sum of b1 and b2, and b3, ((b1+b2)/(b3)) is preferably 0.1 to 9, more preferably 0.14 to 7, further preferably 0.2 to 5.

<13> The cleansing composition according to any one of above <1> to <12>, wherein the content of the component (B) as a salt in the whole composition is preferably 2% by mass or larger, more preferably 5% by mass or larger and is preferably 20% by mass or smaller, more preferably 15% by mass or smaller.

<14> The cleansing composition according to any one of above <1> to <13>, wherein the mass ratio between the component (A) and the component (B), (A)/(B) is preferably 0.0025 or higher, more preferably 0.005 or higher, further preferably 0.02 or higher, even further preferably 0.035 or higher and is preferably 8 or lower, more preferably 1 or lower, further preferably 0.2 or lower.

<15> The cleansing composition according to any one of above <1> to <14>, wherein the content of water as the component (C) in the whole composition is preferably 35% by mass or larger, more preferably 50% by mass or larger, and is preferably 99% by mass or smaller, more preferably 98% by mass or smaller, further preferably 96% by mass or smaller, even further preferably 94% by mass or smaller, far further preferably 90% by mass or smaller, far further preferably 80% by mass or smaller.

<16> The cleansing composition according to any one of above <1> to <15>, further comprising an amphoteric surfactant as a component (D).

<17> The cleansing composition according to <16>, wherein the amphoteric surfactant as the component (D) is preferably an acetic acid betaine-type surfactant, an amine oxide-type surfactant, an imidazolinium betaine-type surfactant, an amide betaine-type surfactant, and a sulfobetaine-type surfactant, more preferably an amide betaine-type surfactant and a sulfobetaine-type surfactant, further preferably lauramidopropyl betaine and/or lauryl hydroxy sulfobetaine.

<18> The cleansing composition according to above <16> or <17>, wherein the content of the component (D) in the whole composition is preferably 0.5 to 30% by mass, more preferably 1% by mass or larger, further preferably 1.5% by mass or larger, even further preferably 2% by mass or larger, far further preferably 3% by mass or larger and is more preferably 15% by mass or smaller, further preferably 10% by mass or smaller.

<19> The cleansing composition according to any one of above <1> to <18>, further comprising a nonionic surfactant having HLB of 11 or higher, preferably HLB of 15 to 17, as a component (E).

<20> The cleansing composition according to above <19>, wherein the nonionic surfactant as the component (E) is preferably polyglycerin fatty acid ester, polyethylene glycol fatty acid ester, polyoxyethylene glycerin fatty acid ester, propylene glycol fatty acid ester, polyoxyethylene polyoxypropylene glycol, sorbitan fatty acid ester, polyoxyethylene sorbitan fatty acid ester, polyoxyethylene sorbit fatty acid ester, polyoxyethylene castor oil, polyoxyethylene hydrogenated castor oil, polyoxyethylene hydrogenated castor oil fatty acid ester, polyalkyl glyceryl ether, polyoxyethylene alkyl ether, polyoxyethylene alkyl ether fatty acid ester, sucrose fatty acid ester, alkyl polyglucoside, and/or alkyl glyceryl ether, more preferably polyoxyethylene sorbitan fatty acid ester and/or alkyl polyglucoside.

<21> The cleansing composition according to above <19> or <20>, wherein the content of the component (E) in the whole composition is preferably 0.5 to 30% by mass, more preferably 1% by mass or larger, further preferably 1.5% by mass or larger, even further preferably 3% by mass or larger and is more preferably 15% by mass or smaller, further preferably 10% by mass or smaller.

<22> The cleansing composition according to any one of above <1> to <21>, further comprising a water-soluble polyvalent metal salt as a component (F).

<23> The cleansing composition according to above <22>, wherein the water-soluble polyvalent metal salt as the component (F) is preferably an inorganic salt of aluminum or an alkaline earth metal such as magnesium, or calcium with halogen or an inorganic acid such as sulfuric acid, sulfonic acid, sulfurous acid, or phosphoric acid or an organic salt of aluminum or the alkaline earth metal with an organic acid such as lactic acid, acetic acid, or malic acid, and is more preferably one or more water-soluble aluminum salts selected from the group consisting of potassium aluminum sulfate (alum), ammonium aluminum sulfate, aluminum chloride, aluminum sulfate, aluminum lactate, and the like, one or more alkaline earth metal salts selected from the group consisting of magnesium sulfate, magnesium chloride, calcium chloride, and the like, further preferably water-soluble polyvalent metal salt(s), even further preferably water-soluble aluminum salt(s).

<24> The cleansing composition according to above <22> or <23>, wherein the mass ratio between the component (A) and the component (F), (A)/(F) is preferably 0.5 to 200, more preferably 1 to 10, further preferably 1.2 to 9.

<25> The cleansing composition according to any one of above <22> to <24>, wherein the mass ratio between the component (B) and the component (F), (B)/(F) is preferably 1 to 200, more preferably 5 to 100, further preferably 8 to 60.

<26> Use of a composition as a skin cleansing agent, the composition comprising the following components (A), (B), and (C):
(A) 0.02% by mass or larger and 10% by mass or smaller of a polymer comprising 85 to 100% by mass of a1 and a2 as constitutional units:
a1: a constitutional unit represented by the formula (1):

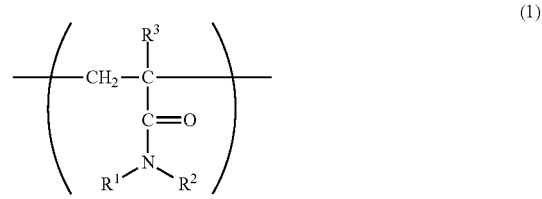

wherein $R^1$ and $R^2$ are the same or different and each represents an alkyl group having 1 to 4 carbon atoms and optionally having a hydroxy group, or a hydrogen atom, and $R^3$ represents a hydrogen atom or a methyl group, and a2: a constitutional unit represented by the formula (2):

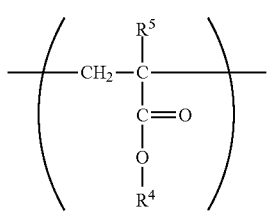
(2)

wherein $R^4$ represents a linear or branched alkyl group having 1 to 22 carbon atoms, and $R^5$ represents a hydrogen atom or a methyl group;
(B) 0.5% by mass or larger and 40% by mass or smaller of an anionic surfactant selected from the group consisting of b1, b2, and b3:

b1: the formula (3):

$$R^6\text{-D-OSO}_3X^1 \qquad (3)$$

wherein $R^6$ represents a linear or branched alkyl group or alkenyl group having 10 to 22 carbon atoms, D represents —$(OCH_2CH_2)_n$—, in which n represents a number of 0 to 10, and $X^1$ represents an alkali metal, an alkaline earth metal, an ammonium, or an organic base, b2: the formula (4):

$$R^7\text{-E-SO}_3X^2 \qquad (4)$$

wherein $R^7$ represents an optionally substituted linear or branched alkyl group or alkenyl group having 10 to 22 carbon atoms, E represents —$(OCH_2CH_2)_m$— or —CO—O—$C_2H_4$—, in which m represents a number of 0 to 10, and $X^2$ represents an alkali metal, an alkaline earth metal, an ammonium, or an organic base, and b3: the formula (5):

$$R^8\text{-G-COOX}^3 \qquad (5)$$

wherein $R^8$ represents a linear or branched alkyl group or alkenyl group having 10 to 22 carbon atoms, G represents —$(OCH_2CH_2)_p$—$OCH_2$— or —CO—NH—$CR^9H$—, in which p represents a number of 0 to 10, and $R^9$ represents a hydrogen atom or a methyl group, and $X^3$ represents an alkali metal, an alkaline earth metal, an ammonium, or an organic base; and
(C) water.
<27> A skin cleansing method comprising applying the cleansing composition according to any one of above <1> to <25> to the skin of the body, followed by rinsing.
<Measurement Method>
(1) Weight-Average Molecular Weight:
The weight-average molecular weight of the polymer as the component (A) was determined by gel permeation chromatography (GPC) measurement. The weight-average molecular weight was determined as a value based on polystyrene. Conditions for the GPC measurement are as follows:
(GPC Measurement Conditions)
Column: two KF-806L columns (manufactured by Showa Denko K.K.) were connected in series for use.
Eluent: laurylamine (1 mmol/L)/$CHCl_3$
Flow rate: 1.0 mL/min.
Measurement temperature: 40° C.
Detector: RI HLC-8320 GPC ECOSEC A calibration curve was prepared using polystyrene (absolute molecular weight: 923,000, 96,400, 30,000, 10,200, and 870).
(2) Monomer Conversion Rate:
The monomer conversion rate after polymerization was determined by liquid chromatography (LC) measurement. The monomer conversion rate was calculated from the peak area ratios of the monomers obtained by the measurement before and after the polymerization.
(Measurement Conditions for Component a1)
Column: L-column ODS (manufactured by CERI)
Measurement temperature: 40° C.
Eluent: water/methanol=90/10 vol %
Flow rate: 1 mL/min.
Detector: UV HITACHI L-7400
Detection wavelength: 220 nm
(Measurement Conditions for Component a2)
Column: L-column ODS (manufactured by CERI)
Measurement temperature: 40° C.
Eluent: water/acetonitrile=10/90 vol %
Flow rate: 1 mL/min.
Detector: UV
Detection wavelength: 210 nm
(3) Compositional Ratio:
The compositional ratio was determined by proton nuclear magnetic resonance (1H-NMR) measurement. Conditions for the 1H-NMR measurement are as given below. The molar ratios of the component a1 and the component a2 were calculated from the peak area ratios of the component a1 and the component a2 obtained by the measurement, and mass a1 and mass a2 of the constitutional units were determined from the values to calculate the value of a1/a2.
(NMR Measurement Conditions)
Measurement solvent: deuterated chloroform
Measurement temperature: 25° C.
Apparatus: NMR 300 MHz manufactured by Varian, Inc.
The number of integrations: 32
Internal standard: None Synthesis of Copolymer Synthesis Example 1 (Copolymer 1)

In a 300-mL separable glass flask, were placed 36.0 g of dimethylacrylamide (DMAA, manufactured by Kohjin Co., Ltd.), 24.0 g of methyl methacrylate (MMA, manufactured by Wako Pure Chemical Industries, Ltd.), and 84.8 g of ethanol, then the mixture was uniformly stirred for 30 minutes under a nitrogen atmosphere. This solution was heated to approximately 78° C. Then, thereto was added a solution containing 0.27 g of dimethyl 2,2'-azobis(isobutyrate) (V-601, manufactured by Wako Pure Chemical Industries, Ltd.) as an initiator in 5.0 g of ethanol. Then, the mixture was allowed to stand at 78° C. for 2 hours for polymerization and for another 4 hours for aging. This reaction solution was cooled and then subjected to reprecipitation with hexane to obtain copolymer 1. The conversion rate of each monomer after the completion of the polymerization was 100%. The obtained copolymer 1 had a weight-average molecular weight of 83,000 and an a1/a2 ratio of 60/40. This copolymer was hardly dissolved in water at 25° C.

Synthesis Example 2 (Copolymer 2)

Copolymer 2 was obtained in the same way as in Synthesis Example 1 except that n-butyl acrylate (BA, manufactured by Wako Pure Chemical Industries, Ltd.) was used in place of MMA. The conversion rate of each monomer after the completion of the polymerization was 100%. The copolymer 2 had a weight-average molecular weight of 47,000 and an a1/a2 ratio of 60/40. This copolymer was hardly dissolved in water at 25° C.

Synthesis Example 3 (Copolymer 3)

Copolymer 3 was obtained in the same way as in Synthesis Example 1 except that: the amount of DMAA added was set to 36.0 g; n-butyl methacrylate (n-BMA, manufactured by Wako Pure Chemical Industries, Ltd.) was used in place of MMA; and the amount of n-BMA added was set to 24.0 g. The conversion rate of each monomer after completion of the polymerization was 100%. The copolymer 3 had a weight-average molecular weight of 89,000 and an a1/a2 ratio of 60/40. This copolymer was hardly dissolved in water at 25° C.

Synthesis Example 4 (Copolymer 4)

Copolymer 4 was obtained in the same way as in Synthesis Example 1 except that t-butyl methacrylate (t-BMA, manufactured by Wako Pure Chemical Industries, Ltd.) was used in place of MMA. The conversion rate of each monomer after completion of the polymerization was 100%. The copolymer 4 had a weight-average molecular weight of 63,000 and an a1/a2 ratio of 60/40. This copolymer was hardly dissolved in water at 25° C.

Synthesis Example 5 (Copolymer 5)

Copolymer 5 was obtained in the same way as in Synthesis Example 1 except that: the amount of DMAA added was set to 48.0 g; lauryl methacrylate (LMA, manufactured by Wako Pure Chemical Industries, Ltd.) was used in place of MMA; and the amount of LMA added was set to 12.0 g. The conversion rate of each monomer after completion of the polymerization was 100%. The copolymer 5 had a weight-average molecular weight of 70,000 and an a1/a2 ratio of 80/20. This copolymer was hardly dissolved in water at 25° C.

Synthesis Example 6 (Copolymer 6)

Copolymer 6 was obtained in the same way as in Synthesis Example 5 except that: the amount of DMAA added was set to 36.0 g; and the amount of LMA added was set to 24.0 g. The conversion rate of each monomer after the completion of the polymerization was 100%. The copolymer 6 had a weight-average molecular weight of 73,000 and an a1/a2 ratio of 60/40. This copolymer was hardly dissolved in water at 25° C.

Synthesis Example 7 (Copolymer 7)

Copolymer 7 was obtained in the same way as in Synthesis Example 5 except that: the amount of DMAA added was set to 24.0 g; and the amount of LMA added was set to 36.0 g. The conversion rate of each monomer after completion of the polymerization was 100%. The copolymer 7 had a weight-average molecular weight of 75,000 and an a1/a2 ratio of 40/60. This copolymer was hardly dissolved in water at 25° C.

Synthesis Example 8 (Copolymer 8)

In a 300-mL separable glass flask, was placed 91.5 g of ethyl acetate (manufactured by KH Neochem Co., Ltd.), and then heated to approximately 78° C. with stirring. Meanwhile, a solution of 16.0 g of DMAA, 64.0 g of LMA, and 1.2 g of V-601 in 9.1 g of ethyl acetate was added to a 300-mL graduated cylinder, and the mixture was stirred at room temperature. After the ethyl acetate reached 78° C., the whole amount of the solution in this graduated cylinder was added dropwise into the separable flask over 4 hours for polymerization and the mixture was allowed to stand for 3 hours for aging. This reaction solution was cooled and then subjected to reprecipitation with hexane to obtain copolymer 8. The conversion rate of each monomer after completion of polymerization was 100%. The copolymer 8 had a weight-average molecular weight of 54,000 and an a1/a2 ratio of 20/80. This copolymer was hardly dissolved in water at 25° C.

Synthesis Example 9 (Copolymer 9)

Copolymer 9 was obtained in the same way as in Synthesis Example 1 except that stearyl methacrylate (SMA, manufactured by Shin-Nakamura Chemical Co., Ltd.) was used in place of MMA. The conversion rate of each monomer after completion of polymerization was 100%. The copolymer 9 had a weight-average molecular weight of 74,000 and an a1/a2 ratio of 60/40. This copolymer was hardly dissolved in water at 25° C.

Synthesis Example 10 (Copolymer 10)

Copolymer 10 was obtained in the same way as in Synthesis Example 5 except that hydroxyethylacrylamide (HEAA, manufactured by Kohjin Co., Ltd.) was used in place of DMAA. The conversion rate of each monomer after completion of polymerization was 100%. The copolymer 10 had a weight-average molecular weight of 70,000 and an a1/a2 ratio of 60/40. This copolymer was hardly dissolved in water at 25° C.

Synthesis Example 11 (Copolymer 11)

Copolymer 11 was obtained in the same way as in Synthesis Example 5 except that t-butylacrylamide (t-BuAA, manufactured by MRC Unitec Co., Ltd.) was used in place of DMAA. The conversion rate of each monomer after completion of polymerization was 100%. The copolymer 11 had a weight-average molecular weight of 81,000 and an a1/a2 ratio of 60/40. This copolymer was hardly dissolved in water at 25° C.

Synthesis Example 12 (Copolymer 12)

In a 300-mL separable glass flask, was placed 147.3 g of isopropanol (IPA, manufactured by Mitsui Chemicals, Inc.), and then heated to approximately 78° C. with stirring. Meanwhile, a solution of 72.0 g of dimethylacrylamide (DMAA, manufactured by Kohjin Co., Ltd.), 48.0 g of lauryl methacrylate (LMA, manufactured by Wako Pure Chemical Industries, Ltd.), and 0.4 g of dimethyl 2,2'-azobis (isobutyrate) (V-601, manufactured by Wako Pure Chemical Industries, Ltd.) in 5.0 g of isopropanol was added to a 300-mL graduated cylinder, and the mixture was stirred at room temperature. After the isopropanol reached 78° C., the whole amount of the solution in this graduated cylinder was added dropwise into the separable flask over 2 hours for polymerization, and the mixture was allowed to stand for 4 hours for aging. This reaction solution was cooled and then subjected to reprecipitation with hexane to obtain copolymer 12. The conversion rate of each monomer after completion of polymerization was 100%. The obtained copolymer 12 had a weight-average molecular weight of 16,000 and an a1/a2 ratio of 60/40. This copolymer was hardly dissolved in water at 25° C.

Synthesis Example 13 (Copolymer 13)

In a 300-mL separable glass flask, was placed 75.6 g of isopropanol (IPA, manufactured by Mitsui Chemicals, Inc.), and then heated to approximately 78° C. with stirring. Meanwhile, a solution of 90.0 g of DMAA, 60.0 g of LMA, and 0.3 g of V-601 in 5.0 g of isopropanol was added to a 300-mL graduated cylinder and the mixture was stirred at room temperature. Copolymer 13 was obtained by the same subsequent synthesis procedures as in the copolymer 12 except that the dropwise addition time was changed to 1 hour. The conversion rate of each monomer after the completion of the polymerization was 100%. The obtained copolymer 13 had a weight-average molecular weight of 45,000 and an a1/a2 ratio of 60/40. This copolymer was hardly dissolved in water at 25° C.

Synthesis Example 14 (Copolymer 14)

In a 300-mL separable glass flask, 75.5 g of isopropanol (IPA, manufactured by Mitsui Chemicals, Inc.) was placed, and then heated to approximately 78° C. with stirring. Meanwhile, a solution of 90.0 g of DMAA, 60.0 g of LMA, and 0.1 g of V-601 in 5.0 g of isopropanol was added to a 300-mL graduated cylinder and mixed at room temperature. Copolymer 14 was obtained by the same subsequent synthesis procedures as in the copolymer 12 except that the dropwise addition time was changed to 1 hour. The conversion rate of each monomer after completion of polymerization was 100%. The obtained copolymer 14 had a weight-average molecular weight of 55,000 and an a1/a2 ratio of 60/40. This copolymer was hardly dissolved in water at 25° C.

Synthesis Example 15 (Copolymer 15)

In a 300-mL separable glass flask, was placed 180.5 g of ethyl acetate (manufactured by KH Neochem Co., Ltd.), and then heated to approximately 78° C. with stirring. Meanwhile, a solution of 48.0 g of DMAA, 32.0 g of LMA, and 1.1 g of V-601 in 5.0 g of ethyl acetate was added to a 300-mL graduated cylinder and the mixture was stirred at room temperature. After the ethyl acetate reached 78° C., the whole amount of the solution in this graduated cylinder was added dropwise into the separable flask over 2 hours for polymerization and the mixture was allowed to stand for another 4 hours for aging. This reaction solution was cooled and then subjected to reprecipitation with hexane to obtain copolymer 15. The conversion rate of each monomer after the completion of the polymerization was 100%. The obtained copolymer 15 had a weight-average molecular weight of 100,000 and an a1/a2 ratio of 60/40. This copolymer was hardly dissolved in water at 25° C.

Synthesis Example 16 (Copolymer 16)

In a 300-mL separable glass flask was placed 159.5 g of ethyl acetate and was heated to approximately 78° C. with stirring. Meanwhile, in a 300-mL graduated cylinder was added a solution of 78.0 g of DMAA, 52.0 g of LMA, and 1.0 g of V-601 dissolved in 5.0 g of ethyl acetate and the mixture was stirred at room temperature. After the ethyl acetate reached 78° C., the whole amount of the solution in this graduated cylinder was added dropwise into the separable flask over 4 hours for polymerization and the mixture was allowed to stand for another 4 hours for aging. This reaction solution was cooled and then subjected to reprecipitation with hexane to obtain copolymer 16. The conversion rate of each monomer after the completion of the polymerization was 100%. The obtained copolymer 16 had a weight-average molecular weight of 180,000 and an a1/a2 ratio of 60/40. This copolymer was hardly dissolved in water at 25° C.

Synthesis Example 17 (Copolymer 17)

In a 300-mL separable glass flask was placed 181.4 g of ethyl acetate, and heated to approximately 78° C. with stirring. Meanwhile, a solution of 48.0 g of DMAA, 32.0 g of LMA, and 0.3 g of V-601 in 5.0 g of ethyl acetate was added to a 300-mL graduated cylinder and the mixture was stirred at room temperature. Copolymer 17 was obtained by the same subsequent synthesis procedures as in the copolymer 14. The conversion rate of each monomer after completion of polymerization was 100%. The obtained copolymer 17 had a weight-average molecular weight of 320,000 and an a1/a2 ratio of 60/40. This copolymer was hardly dissolved in water at 25° C.

Synthesis Example 18 (Copolymer 18)

In a 300-mL separable glass flask was placed 142.3 g of ethyl acetate and heated to approximately 78° C. with stirring. Meanwhile, in a 300-mL graduated cylinder was added a solution of 72.0 g of DMAA, 48.0 g of LMA, and 0.4 g of V-601 in 5.0 g of ethyl acetate and the mixture was stirred at room temperature. Copolymer 18 was obtained by the same subsequent synthesis procedures as in the copolymer 14. The conversion rate of each monomer after completion of polymerization was 100%. The obtained copolymer 18 had a weight-average molecular weight of 480,000 and an a1/a2 ratio of 60/40. This copolymer was hardly dissolved in water at 25° C.

The amounts of the components mixed for polymerization, the compositional ratio, the molecular weight, etc., of each copolymer are summarized in Table 1.

TABLE 1

| | | Copolymer No. | | | | | | | | | |
|---|---|---|---|---|---|---|---|---|---|---|---|
| | | 1 | 2 | 3 | 4 | 5 | 6 | 7 | 8 | 9 | 10 |
| Hydrophilic constitutional unit (g) a1 | DMAA | 36.0 | 36.0 | 36.0 | 36.0 | 48.0 | 36.0 | 24.0 | 16.0 | 36.0 | — |
| | HEAA | — | — | — | — | — | — | — | — | — | 36.0 |
| | t-BuAA | — | — | — | — | — | — | — | — | — | — |

TABLE 1-continued

|  |  | | | | | | | | | | |
|---|---|---|---|---|---|---|---|---|---|---|---|
| Hydrophobic constitutional unit (g) a2 | MMA | 24.0 | — | — | — | — | — | — | — | — | — |
|  | BA | — | 24.0 | — | — | — | — | — | — | — | — |
|  | BMA | — | — | 24.0 | — | — | — | — | — | — | — |
|  | t-BMA | — | — | — | 24.0 | — | — | — | — | — | — |
|  | LMA | — | — | — | — | 12.0 | 24.0 | 36.0 | 64.0 | — | 24.0 |
|  | SMA | — | — | — | — | — | — | — | — | 24.0 | — |
| Polymerization initiator (g) | V-601 | 0.27 | 0.25 | 0.25 | 0.25 | 0.24 | 0.21 | 0.18 | 1.20 | 0.20 | 0.19 |
| Solvent (g) (of the upper amount, for dissolution of the initiator) |  | ethanol 89.8 (5.0) | ethanol 89.8 (5.0) | ethanol 89.8 (5.0) | ethanol 89.3 (5.0) | ethanol 89.8 (5.0) | ethanol 89.8 (5.0) | ethanol 89.8 (5.0) | ethyl acetate 100.6 (5.0) | ethanol 89.8 (5.0) | ethanol 89.8 (5.0) |
| Polymerization concentration (mass %) |  | 40 | 40 | 40 | 40 | 40 | 40 | 40 | 44 | 40 | 40 |
| Weight-average molecular weight |  | 83,000 | 47,000 | 89,000 | 63,000 | 70,000 | 73,000 | 75,000 | 54,000 | 74,000 | 70,000 |
| a1/a2 |  | 60/40 | 60/40 | 60/40 | 60/40 | 80/20 | 60/40 | 40/60 | 20/80 | 60/40 | 60/40 |

|  |  |  | Copolymer No. | | | | | | | |
|---|---|---|---|---|---|---|---|---|---|---|
|  |  |  | 11 | 12 | 13 | 14 | 15 | 16 | 17 | 18 |
| Hydrophilic constitutional unit (g) a1 | DMAA | | — | 72.0 | 90.0 | 90.0 | 48.0 | 78.0 | 48.0 | 72.0 |
|  | HEAA | | — | — | — | — | — | — | — | — |
|  | t-BuAA | | 36.0 | — | — | — | — | — | — | — |
| Hydrophobic constitutional unit (g) a2 | MMA | | — | — | — | — | — | — | — | — |
|  | BA | | — | — | — | — | — | — | — | — |
|  | BMA | | — | — | — | — | — | — | — | — |
|  | t-BMA | | — | — | — | — | — | — | — | — |
|  | LMA | | 24.0 | 48.0 | 60.0 | 60.0 | 32.0 | 52.0 | 32.0 | 48.0 |
|  | SMA | | — | — | — | — | — | — | — | — |
| Polymerization initiator (g) | V-601 | | 0.17 | 0.40 | 0.30 | 0.10 | 1.10 | 1.00 | 0.30 | 0.40 |
| Solvent (g) (of the upper amount, for dissolution of the initiator) | | | ethanol 89.8 (5.0) | IPA 152.3 (5.0) | IPA 80.5 (5.0) | IPA 80.6 (5.0) | ethyl acetate 185.5 (5.0) | ethyl acetate 164.5 (5.0) | ethyl acetate 186.4 (5.0) | ethyl acetate 147.3 (5.0) |
| Polymerization concentration (mass %) | | | 40 | 44 | 65 | 65 | 30 | 44 | 30 | 44 |
| Weight-average molecular weight | | | 81,000 | 16,000 | 45,000 | 55,000 | 100,000 | 180,000 | 320,000 | 480,000 |
| a1/a2 | | | 60/40 | 60/40 | 60/40 | 60/40 | 60/40 | 60/40 | 60/40 | 60/40 |

EXAMPLES

Examples 1 to 33 and Comparative Examples 1 to 4

Each cleansing composition shown in Table 2 or 3 was produced. The obtained cleansing composition was evaluated for foaming quickness, foam quality upon cleansing, foam volume upon cleansing, feeling of foam thickness upon cleansing, absence of feeling of residues on the skin at the completion of rinsing, strength of stop feeling at the completion of rinsing, skin feel immediately after towel-drying, and skin feel after drying (natural bare skin feeling free from feeling of residues on the skin and smooth and moist feeling of the skin free from powdery texture). The results are also shown in Tables 2 and 3.

(Production Method)

The component (B) and the component (C) are mixed and heated to 70° C. or higher. The component (D) and the component (E) are optionally added thereto, and a homogeneous mixture is obtained. An appropriate amount of sodium hydroxide or malic acid is added thereto as a pH adjuster to adjust the pH of a 20-fold dilution to within the prescribed range. To this solution, are added the component (A) and other polymers, and other components, and the mixture is further stirred. The resulting homogeneous mixture was cooled to 30° C. to obtain a cleansing composition.

(Evaluation Method)

(1) Foaming Quickness:

1 g of each cleansing composition was put on a palm, then diluted approximately 5-fold with tap water at 30° C., and lightly foamed with both hands for 5 seconds. Its foaming quickness was evaluated. The evaluation was carried out according to the following criteria and indicated by an average of scores given by 5 expert panelists:

5: very quick foaming (property) was felt.
4: quick foaming (property) was felt.
3: normal (ordinary-level) foaming (property) was felt.
2: poor foaming was felt.
1: foaming was not felt at all.

(2) Foam Quality (Creaminess) Upon Cleansing:

1 g of each cleansing composition was put on a palm, then diluted approximately 5-fold with tap water at 30° C., and lightly foamed with both hands for 20 seconds. Its foam quality (creaminess) was evaluated. The evaluation was carried out according to the following criteria and indicated by an average of scores given by 5 expert panelists:

5: fine, very creamy, and favorable foam quality was felt.
4: creamy and favorable foam quality was felt.
3: slightly creamy foam quality was felt.
2: slightly rough foam quality was felt.
1: rough foam quality was felt.

(3) Foam Volume Upon Cleansing:

1 g of each cleansing composition was put on a palm, then diluted 5-fold with tap water, and lightly foamed with both hands for 20 seconds. In this respect, the foam volume was evaluated. The evaluation was carried out according to the following criteria and indicated by an average of scores given by 5 expert panelists:

5: a very large foam volume was felt.
4: a large foam volume was felt.
3: a normal foam volume was felt.
2: a slightly small foam volume was felt.
1: a small foam volume was felt.

(4) Feeling of Foam Thickness Upon Cleansing:

1 g of each cleansing composition was put on a palm, then diluted 5-fold with tap water, and lightly foamed with both hands for 20 seconds. Feeling of foam thickness was evaluated when the foam was softly pressed between both palms. The evaluation was carried out according to the following criteria and indicated by an average of scores given by 5 expert panelists:

5: very thick foam was felt.
4: thick foam was felt.
3: slightly less thick foam was felt.
2: less thick foam was felt.
1: thick foam was not felt at all.

(5) Absence of Feeling of Residues on Skin at Completion of Rinsing:

1 g of each cleansing composition was put on a palm, then diluted approximately 5-fold with tap water at 30° C., and lightly foamed with both hands for 20 seconds. The foam was spread throughout one arm (from the elbow to the wrist) and rinsed with tap water. This rinsing was carried out by rubbing both forearms with each other. Absence of feeling of residues on the skin upon the completion of rinsing was evaluated. The evaluation was carried out according to the following criteria, and the evaluation results were indicated by an average of scores given by 5 expert panelists:

5: no feeling of residues was received on the skin.
4: little feeling of residues was received on the skin.
3: slight feeling of residues was received on the skin.
2: feeling of residues was received on the skin.
1: strong feeling of residues was received on the skin.

(6) Strength of Stop Feeling (Feeling with Frictional Resistance which Indicates Completion of Washing Off) at Completion of Rinsing:

1 g of each cleansing composition was put on a palm, then diluted approximately 5-fold with tap water at 30° C., and lightly foamed with both hands for 20 seconds. The foam was spread throughout one arm (from the elbow to the wrist) and rinsed with tap water. This rinsing was carried out by rubbing both forearms with each other. Rinsability was evaluated on the basis of a level of stop feeling at the completion of rinsing. The evaluation was carried out according to the following criteria, and the evaluation results were indicated by an average of scores given by five expert panelists:

5: stop feeling was strongly received.
4: stop feeling was received.
3: stop feeling was slightly received.
2: stop feeling was hardly received.
1: stop feeling was absent.

(7) Skin Feel Immediately after Towel-Drying:

1 g of each cleansing composition was put on a palm, then diluted approximately 5-fold with tap water at 30° C., and lightly foamed with both hands for 20 seconds. The foam was spread throughout one arm (from the elbow to the wrist) and rinsed with tap water. Then, the arm was toweled, and immediately thereafter, skin feel during being dried immediately after toweling was evaluated. The evaluation was carried out according to the following criteria, and the evaluation results were indicated by an average of scores given by 5 expert panelists:

3: sticky feeling was hardly received during the drying of the skin.
2: sticky feeling was slightly received during the drying of the skin.
1: sticky feeling was received during the drying of the skin.

(8) Skin Feel after Drying (Natural Bare Skin Feeling without Feeling of Residues on Skin):

Ten expert panelists cleansed their whole bodies using each cleansing composition. The number of panelists is shown in the tables who answered that they had received natural bare skin feeling without feeling of residues as to the skin 5 minutes after towel-drying.

(9) Skin Feel after Drying (Smooth and Moist Skin Feel without Powdery Texture):

Ten expert panelists cleansed their whole bodies using each cleansing composition. The number of panelists is shown in the tables who answered that they had received smooth and moist skin feel without powdery texture as to the skin 5 minutes after towel-drying.

TABLE 2

| Component (mass %) | Example | | | | | | | | | |
|---|---|---|---|---|---|---|---|---|---|---|
| | 1 | 2 | 3 | 4 | 5 | 6 | 7 | 8 | 9 | 10 |
| (A) Copolymer 1 (DMAA/MMA = 6/4)Mw = 83,000 | | | | | | | | | | |
| Copolymer 2 (DMAA/BA = 6/4)Mw = 47,000 | | | | | | | | | | |
| Copolymer 3 (DMAA/BMA = 6/4)Mw = 89,000 | | | | | | | | | | |
| Copolymer 4 (DMAA/t-BMA-6/4)Mw = 63,000 | | | | | | | | | | |
| Copolymer 5 (DMAA/LMA = 8/2)Mw = 70,000 | | | | | | | | | | |
| Copolymer 6 (DMAA/LMA = 6/4)Mw = 73,000 | 0.40 | 0.40 | 0.40 | 0.40 | 0.40 | 0.40 | 4.00 | 2.00 | 1.00 | 0.40 |
| Copolymer 7 (DMAA/LMA = 4/6)Mw = 75,000 | | | | | | | | | | |

TABLE 2-continued

| Component (mass %) | | | | | | | | | | |
|---|---|---|---|---|---|---|---|---|---|---|
| Copolymer 8 (DMAA/LMA = 2/8)Mw = 54,000 | | | | | | | | | | |
| Copolymer 9 (DMAA/SMA = 6/4)Mw = 74,000 | | | | | | | | | | |
| Copolymer 10 (HEAA/LMA = 6/4)Mw = 70,000 | | | | | | | | | | |
| Copolymer 11 (t-BuAA/LMA = 6/4)Mw = 81,000 | | | | | | | | | | |
| Copolymer 12 (DMAA/LMA = 6/4)Mw = 16,000 | | | | | | | | | | |
| Copolymer 13 (DMAA/LMA = 6/4)Mw = 45,000 | | | | | | | | | | |
| Copolymer 14 (DMAA/LMA = 6/4)Mw = 55,000 | | | | | | | | | | |
| Copolymer 15 (DMAA/LMA = 6/4)Mw = 100,000 | | | | | | | | | | |
| Copolymer 16 (DMAA/LMA = 6/4)Mw = 180,000 | | | | | | | | | | |
| Copolymer 17 (DMAA/LMA = 6/4)Mw = 320,000 | | | | | | | | | | |
| Copolymer 18 (DMAA/LMA = 6/4)Mw = 480,000 | | | | | | | | | | |
| Acrylic acid/ethyl acrylate/n-t-butylacrylamide copolymer *1 | | | | | | | | | | |
| (B) Sodium polyoxyethylene(2) lauryl ether sulfate *2 | 5.00 | | | | | 0.50 | 2.00 | 5.00 | 10.00 | |
| Ammonium polyoxyethylene(1) alkyl ether sulfate *3 | | 5.00 | | | | | | | | |
| Sodium alpha-olefin sulfonate *4 | | | 5.00 | | | | | | | |
| Sodium polyoxyethylene(2.6) lauryl ether carboxylate *5 | | | | 5.00 | | | | | | |
| Sodium polyoxyethylene(4.5) lauryl ether carboxylate *6 | | | | | 5.00 | | | | | |
| Sodium salt of N-cocoyl-L-alanine *7 | | | | | | 5.00 | | | | |
| (C) Water | balance | balance | balance | balance | balance | balance | balance | balance | balance | balance |
| (D) Lauryl hydroxy sulfobetaine *8 | | | | | | | | | | |
| (E) Alkyl (C10-16) polyglucoside *9 | | | | | | | | | | |
| Homopolymer of dimethyl diallyl ammonium chloride *10 | | | | | | | | | | |
| Polyethylene glycol *11 | | | | | | | | | | |
| Hydroxypropylmethylcellulose *12 | | | | | | | | | | |
| Sodium chloride | | | | | | | | | | |
| pH adjuster (malic acid) | q.s. | | q.s. | q.s. | | q.s. | q.s. | q.s. | q.s. | q.s. |
| pH adjuster (NaOH) | | | | | | | | | | |
| Total | 100 | 100 | 100 | 100 | 100 | 100 | 100 | 100 | 100 | 100 |
| (A)/(B) mass ratio | 0.080 | 0.080 | 0.080 | 0.080 | 0.080 | 0.080 | 8.000 | 1.000 | 0.200 | 0.040 |
| pH (20-fold dilution) | 6.9 | 6.9 | 8.1 | 5.8 | 6.0 | 8.3 | 6.9 | 6.9 | 7.0 | 6.9 |
| Foaming quickness | 3.8 | 3.8 | 3.8 | 3.8 | 3.8 | 3.6 | 3 | 3.4 | 3.8 | 4.2 |
| Foam quality upon cleansing | 4.2 | 4.2 | 4 | 4.6 | 4.6 | 4.6 | 3.6 | 4 | 4.2 | 4.2 |
| Foam volume upon cleansing | 4.4 | 4.4 | 4.2 | 4 | 4 | 4.2 | 3.2 | 3.8 | 4.4 | 4.6 |
| Feeling of foam thickness upon cleansing | 3.4 | 3.4 | 3.2 | 3.6 | 3.6 | 3.6 | 2.6 | 2.8 | 3.4 | 3.4 |
| Absence of feeling of residues on skin at completion of rinsing | 4.8 | 4.6 | 4.6 | 4.8 | 4.8 | 4 | 4.2 | 4.4 | 4.6 | 4.6 |
| Strength of stop feeling at completion of rinsing | 4.4 | 4.4 | 4.6 | 4.6 | 4.6 | 4.8 | 4.6 | 4.6 | 4.6 | 4.2 |
| Skin feel immediately after towel-drying | 2.8 | 3 | 2.8 | 2.8 | 2.8 | 2.4 | 2.4 | 2.6 | 2.8 | 2.8 |
| Skin feel after drying (natural bare skin feeling without feeling of residues on skin) | 9 | 8 | 8 | 9 | 8 | 6 | 7 | 8 | 9 | 8 |
| Skin feel after drying (smooth and moist feeling of skin without powdery texture) | 8 | 8 | 8 | 7 | 7 | 6 | 9 | 8 | 8 | 8 |

| | Example | | | | | | | | |
|---|---|---|---|---|---|---|---|---|---|
| Component (mass %) | 11 | 12 | 13 | 14 | 15 | 16 | 17 | 18 | 19 |
| (A) Copolymer 1 (DMAA/MMA = 6/4)Mw = 83,000 | | | | | 0.40 | | | | |
| Copolymer 2 (DMAA/BA = 6/4)Mw = 47,000 | | | | | | 0.40 | | | |
| Copolymer 3 (DMAA/BMA = 6/4)Mw = 89,000 | | | | | | | 0.40 | | |
| Copolymer 4 (DMAA/t-BMA-6/4)Mw = 63,000 | | | | | | | | 0.40 | |

TABLE 2-continued

| | 1 | 2 | 3 | 4 | 5 | 6 | 7 | 8 | 9 |
|---|---|---|---|---|---|---|---|---|---|
| Copolymer 5 (DMAA/LMA = 8/2)Mw = 70,000 | | | | | | | | | 0.40 |
| Copolymer 6 (DMAA/LMA = 6/4)Mw = 73,000 | 0.40 | 0.10 | | | | | | | |
| Copolymer 7 (DMAA/LMA = 4/6)Mw = 75,000 | | | | | | | | | 0.40 |
| Copolymer 8 (DMAA/LMA = 2/8)Mw = 54,000 | | | | | | | | | |
| Copolymer 9 (DMAA/SMA = 6/4)Mw = 74,000 | | | | | | | | | |
| Copolymer 10 (HEAA/LMA = 6/4)Mw = 70,000 | | | | | | | | | |
| Copolymer 11 (t-BuAA/LMA = 6/4)Mw = 81,000 | | | | | | | | | |
| Copolymer 12 (DMAA/LMA = 6/4)Mw = 16,000 | | | | | | | | | |
| Copolymer 13 (DMAA/LMA = 6/4)Mw = 45,000 | | | | | | | | | |
| Copolymer 14 (DMAA/LMA = 6/4)Mw = 55,000 | | | | | | | | | |
| Copolymer 15 (DMAA/LMA = 6/4)Mw = 100,000 | | | | | | | | | |
| Copolymer 16 (DMAA/LMA = 6/4)Mw = 180,000 | | | | | | | | | |
| Copolymer 17 (DMAA/LMA = 6/4)Mw = 320,000 | | | | | | | | | |
| Copolymer 18 (DMAA/LMA = 6/4)Mw = 480,000 | | | | | | | | | |
| Acrylic acid/ethyl acrylate/n-t-butylacrylamide copolymer *1 | | | 0.20 | | | | | | |
| (B) Sodium polyoxyethylene(2) lauryl ether sulfate *2 | 15.00 | 20.00 | 5.00 | 5.00 | 5.00 | 5.00 | 5.00 | 5.00 | 5.00 |
| Ammonium polyoxyethylene(1) alkyl ether sulfate *3 | | | | | | | | | |
| Sodium alpha-olefin sulfonate *4 | | | | | | | | | |
| Sodium polyoxyethylene(2.6) lauryl ether carboxylate *5 | | | | | | | | | |
| Sodium polyoxyethylene(4.5) lauryl ether carboxylate *6 | | | | | | | | | |
| Sodium salt of N-cocoyl-L-alanine *7 | | | | | | | | | |
| (C) Water | balance | balance | balance | balance | balance | balance | balance | balance | balance |
| (D) Lauryl hydroxy sulfobetaine *8 | | | | | | | | | |
| (E) Alkyl (C10-16) polyglucoside *9 | | | | | | | | | |
| Homopolymer of dimethyl diallyl ammonium chloride *10 | | | | | | | | | |
| Polyethylene glycol *11 | | | | | | | | | |
| Hydroxypropylmethylcellulose *12 | | | | | | | | | |
| Sodium chloride | | | | | | | | | |
| pH adjuster (malic acid) | q.s. | q.s. | q.s. | q.s. | q.s. | q.s. | q.s. | q.s. | q.s. |
| pH adjuster (NaOH) | | | q.s. | | | | | | |
| Total | 100 | 100 | 100 | 100 | 100 | 100 | 100 | 100 | 100 |
| (A)/(B) mass ratio | 0.027 | 0.005 | 0.040 | 0.080 | 0.080 | 0.080 | 0.080 | 0.080 | 0.080 |
| pH (20-fold dilution) | 6.8 | 6.8 | 8.7 | 6.8 | 6.8 | 6.8 | 6.9 | 6.8 | 6.8 |
| Foaming quickness | 4.4 | 4.4 | 3.6 | 3.8 | 3.8 | 3.8 | 3.6 | 3.6 | 3.6 |
| Foam quality upon cleansing | 3.8 | 3.6 | 3.8 | 4.2 | 4.2 | 4.2 | 4 | 4 | 4 |
| Foam volume upon cleansing | 4.8 | 4.8 | 4.2 | 4.4 | 4.4 | 4.4 | 4.2 | 4.2 | 4.4 |
| Feeling of foam thickness upon cleansing | 3.4 | 3.4 | 3 | 3.4 | 3.4 | 3.4 | 3.2 | 3.2 | 3.2 |
| Absence of feeling of residues on skin at completion of rinsing | 4.6 | 4.4 | 4.4 | 4.6 | 4.8 | 4.8 | 4.6 | 4.8 | 4.8 |
| Strength of stop feeling at completion of rinsing | 3.8 | 3.6 | 4.4 | 4 | 4 | 4.4 | 4.4 | 4.4 | 4.4 |
| Skin feel immediately after towel-drying | 2.4 | 2.4 | 2.8 | 2.6 | 2.6 | 2.8 | 2.6 | 2.8 | 2.8 |
| Skin feel after drying (natural bare skin feeling without feeling of residues on skin) | 7 | 6 | 7 | 7 | 7 | 8 | 8 | 8 | 9 |

TABLE 2-continued

| | | | | | | | | | |
|---|---|---|---|---|---|---|---|---|---|
| Skin feel after drying (smooth and moist feeling of skin without powdery texture) | 7 | 7 | 7 | 8 | 8 | 7 | 7 | 8 | 8 |

*1 Active component (containing approximately 9.5% of acrylic acid) of Ultrahold Strong manufactured by BASF Ltd.
*2 Active component of EMAL 125A manufactured by Kao Corp.
*3 Active component of EMAL 227 manufactured by Kao Corp.
*4 Active component of K LIPOLAN PJ-400 manufactured by Lion Corp.
*5 Active component of AKYPO LM-26SD manufactured by Kao Corp.
*6 Active component of KAO AKYPO RLM-45NV manufactured by Kao Corp.
*7 Active component of Amilite GCK-12B manufactured by Ajinomoto Co., Inc.
*8 Active component of AMPHITOL 20HD manufactured by Kao Corp.
*9 Active component of AG-124 manufactured by Kao Corp.
*10 Active component of Merquat 100 manufactured by ONDEO Nalco Co., Ltd.
*11 Active component of ALKOX E-100 manufactured by Meisei Chemical Works, Ltd.
*12 Active component of Metolose 60SH-10000 manufactured by Shin-Etsu Chemical Co., Ltd.

TABLE 3

| Component (mass %) | Example | | | | | | | | | | | | | | Comparative Example | | | |
|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 1 | 2 | 3 | 4 |
| (A) Copolymer 1 (DMAA/MMA = 6/4)Mw = 83,000 | | | | | | | | | | | | | | | | | | |
| Copolymer 2 (DMAA/BA = 6/4)Mw = 47,000 | | | | | | | | | | | | | | | | | | |
| Copolymer 3 (DMAA/BMA = 6/4)Mw = 89,000 | | | | | | | | | | | | | | | | | | |
| Copolymer 4 (DMAA/t-BMA = 6/4)Mw = 63,000 | | | | | | | | | | | | | | | | | | |
| Copolymer 5 (DMAA/LMA = 8/2)Mw = 70,000 | | | | | | | | | | | | | | | | | | |
| Copolymer 6 (DMAA/LMA = 6/4)Mw = 73,000 | | | | | | | | | | | | 0.40 | 0.40 | 0.40 | | | | |
| Copolymer 7 (DMAA/LMA = 4/6)Mw = 75,000 | | | | | | | | | | | | | | | | | | |
| Copolymer 8 (DMAA/LMA = 2/8)Mw = 54,000 | 0.15 | | | | | | | | | | | | | | | | | |
| Copolymer 9 (DMAA/SMA = 6/4)Mw = 74,000 | | 0.40 | | | | | | | | | | | | | | | | |
| Copolymer 10 (HEAA/LMA = 6/4)Mw = 70,000 | | | 0.40 | | | | | | | | | | | | | | | |
| Copolymer 11 (t-BuAA/LMA = 6/4)Mw = 81,000 | | | | 0.40 | | | | | | | | | | | | | | |
| Copolymer 12 (DMAA/LMA = 6/4)Mw = 16,000 | | | | | 0.40 | | | | | | | | | | | | | |
| Copolymer 13 (DMAA/LMA = 6/4)Mw = 45,000 | | | | | | 0.40 | | | | | | | | | | | | |
| Copolymer 14 (DMAA/LMA = 6/4)Mw = 55,000 | | | | | | | 0.40 | | | | | | | | | | | |
| Copolymer 15 (DMAA/LMA = 6/4)Mw = 100,000 | | | | | | | | 0.40 | | | | | | | | | | |
| Copolymer 16 (DMAA/LMA = 6/4)Mw = 180,000 | | | | | | | | | 0.40 | | | | | | | | | |
| Copolymer 17 (DMAA/LMA = 6/4)Mw = 320,000 | | | | | | | | | | 0.40 | | | | | | | | |
| Copolymer 18 (DMAA/LMA = 6/4)Mw = 480,000 | | | | | | | | | | | 0.40 | | | | | | | |
| Acrylic acid/ethyl acrylate/n-t-butylacrylamide copolymer *1 | | | | | | | | | | | | | | | | | | |

TABLE 3-continued

| Component (mass %) | Example | | | | | | | | | | | | | | Comparative Example | | | |
|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 1 | 2 | 3 | 4 |
| (B) Sodium polyoxyethylene(2) lauryl ether sulfate *2 | 10.00 | 5.00 | 5.00 | 5.00 | 5.00 | 5.00 | 5.00 | 5.00 | 5.00 | 5.00 | 5.00 | 5.00 | 5.00 | 5.00 | 5.00 | 5.00 | 5.00 | 5.00 |
| Ammonium polyoxyethylene(1) alkyl ether sulfate *3 | | | | | | | | | | | | | | | | | | |
| Sodium alpha-olefin sulfonate *4 | | | | | | | | | | | | | | | | | | |
| Sodium polyoxyethylene(2.6) lauryl ether carboxylate *5 | | | | | | | | | | | | | | | | | | |
| Sodium polyoxyethylene(4.5) lauryl ether carboxylate *6 | | | | | | | | | | | | | | | | | | |
| Sodium salt of N-cocoyl-L-alanine *7 | | | | | | | | | | | | | | | | | | |
| (C) Water | balance | balance | balance | balance | balance | balance | balance | balance | balance | balance | balance | balance | balance | balance | balance | balance | balance | balance |
| (D) Lauryl hydroxy sulfobetaine *8 | | | | | | | | | | | | 3.00 | | 3.00 | | | | |
| (E) Alkyl (C10-16) polyglucoside *9 | | | | | | | | | | | | | 3.00 | 3.00 | | | | |
| Homopolymer of dimethyl diallyl ammonium chloride *10 | | | | | | | | | | | | | | | | 0.40 | | |
| Polyethylene glycol *11 | | | | | | | | | | | | | | | | | 0.40 | |
| Hydroxypropylmethylcellulose *12 | | | | | | | | | | | | | | | | 2.00 | | 0.40 |
| Sodium chloride | q.s. | q.s. | q.s. | q.s. | q.s. | q.s. | q.s. | q.s. | q.s. | q.s. | q.s. | q.s. | q.s. | q.s. | q.s. | q.s. | q.s. | q.s. |
| pH adjuster (malic acid) | | | | | | | | | | | | | | q.s. | | | | |
| pH adjuster (NaOH) | | | | | | | | | | | | | | | | | | |
| Total | 100 | 100 | 100 | 100 | 100 | 100 | 100 | 100 | 100 | 100 | 100 | 100 | 100 | 100 | 100 | 100 | 100 | 100 |
| (A)/(B) mass ratio | 0.015 | 0.080 | 0.080 | 0.080 | 0.080 | 0.080 | 0.080 | 0.080 | 0.080 | 0.080 | 0.080 | 0.080 | 0.080 | 0.080 | 0.000 | 0.080 | 0.080 | 0.080 |
| pH (20-fold dilution) | 6.8 | 7.1 | 6.8 | 7.0 | 6.8 | 6.9 | 6.9 | 6.8 | 6.8 | 6.8 | 6.9 | 6.3 | 6.8 | 6.6 | 6.8 | 6.5 | 6.7 | 6.8 |
| Foaming quickness | 4 | 3.8 | 3.6 | 3.6 | 3.6 | 3.8 | 3.8 | 3.8 | 3.8 | 3.8 | 3.8 | 3.8 | 4 | 4.4 | 3.6 | 3.4 | 3.2 | 3.6 |
| Foam quality upon cleansing | 3.8 | 4.2 | 4 | 4 | 3.8 | 4.2 | 4.2 | 4.2 | 4.2 | 4.4 | 4.4 | 4.8 | 4.6 | 4.6 | 2.8 | 2.4 | 4.4 | 3.2 |
| Foam volume upon cleansing | 4.6 | 4.4 | 4.2 | 4.2 | 4.4 | 4.2 | 4.4 | 4.4 | 4.4 | 4.4 | 4.4 | 4.4 | 4.6 | 4.6 | 4 | 3.6 | 4 | 4.2 |
| Feeling of foam thickness upon cleansing | 3.4 | 3.4 | 3.2 | 3.2 | 3 | 3.2 | 3.2 | 3.4 | 3.4 | 3.4 | 3.4 | 3.8 | 3.6 | 4.2 | 3 | 2.8 | 4 | 3.2 |
| Absence of feeling of residues on skin at completion of rinsing | 4.4 | 4.6 | 4.6 | 4.8 | 4.6 | 4.4 | 4.8 | 4.8 | 4.4 | 4.8 | 4.6 | 4.8 | 4.8 | 4.8 | 3.2 | 1.4 | 2.2 | 1.8 |
| Strength of stop feeling at completion of rinsing | 4 | 4.4 | 4.2 | 4.2 | 4.4 | 4.4 | 4.4 | 4.4 | 4.4 | 4.4 | 4.4 | 4.4 | 4.4 | 4.4 | 3.2 | 4.8 | 3.2 | 3.4 |
| Skin feel immediately after towel-drying | 2.8 | 2.6 | 2.8 | 2.8 | 2.8 | 2.8 | 2.8 | 2.8 | 2.6 | 2.6 | 2.6 | 2.8 | 2.6 | 2.8 | 2.4 | 1.4 | 1.6 | 2.2 |
| Skin feel after drying (natural bare skin feeling without feeling of residues on skin) | 7 | 7 | 9 | 8 | 7 | 8 | 9 | 9 | 9 | 8 | 7 | 9 | 9 | 9 | 5 | 2 | 4 | 3 |

TABLE 3-continued

| Component (mass %) | Example | | | | | | | | | | | | | | Comparative Example | | | |
|---|---|---|---|---|---|---|---|---|---|---|---|---|---|---|---|---|---|---|
| | 20 | 21 | 22 | 23 | 24 | 25 | 26 | 27 | 28 | 29 | 30 | 31 | 32 | 33 | 1 | 2 | 3 | 4 |
| Skin feel after drying (smooth and moist feeling of skin without powdery texture) | 8 | 7 | 7 | 7 | 8 | 8 | 8 | 8 | 8 | 8 | 8 | 8 | 8 | 8 | 7 | 3 | 7 | 5 |

*1 Active component (containing approximately 9.5% of acrylic acid) of Ultrahold Strong manufactured by BASF Ltd.
*2 Active component of EMAL 125A manufactured by Kao Corp.
*3 Active component of EMAL 227 manufactured by Kao Corp.
*4 Active component of K LIPOLAN PJ-400 manufactured by Lion Corp.
*5 Active component of AKYPO LM-26SD manufactured by Kao Corp.
*6 Active component of KAO AKYPO RLM-45NV manufactured by Kao Corp.
*7 Active component of Amilite GCK-12B manufactured by Ajinomoto Co., Inc.
*8 Active component of AMPHITOL 20HD manufactured by Kao Corp.
*9 Active component of AG-124 manufactured by Kao Corp.
*10 Active component of Merquat 100 manufactured by ONDEO Nalco Co., Ltd.
*11 Active component of ALKOX E-100 manufactured by Meisei Chemical Works, Ltd.
*12 Active component of Metolose 60SH-10000 manufactured by Shin-Etsu Chemical Co., Ltd.

Examples 34 to 54

In the same way as in Examples 1 to 33, each cleansing composition shown in Table 4 was produced and evaluated for foaming quickness, foam quality upon cleansing, foam volume upon cleansing, feeling of foam thickness upon cleansing, the absence of feeling of residues on the skin at the completion of rinsing, strength of stop feeling at the completion of rinsing, skin feel immediately after towel-drying, and skin feel after drying (natural bare skin feeling without feeling of residues on the skin and smooth and moist feeling of the skin without powdery texture). Also, the absence of sliminess at the initial stage of rinsing was evaluated. The results are also shown in Table 4.

(Evaluation Method) Absence of Sliminess at Initial Stage of Rinsing:

1 g of each cleansing composition was put on a palm, then diluted approximately 5-fold with tap water at 30° C., and lightly foamed with both hands for 20 seconds. The foam was spread throughout one arm for cleansing. The cleansed arm was rinsed by pouring 50 mL of tap water placed in DesCup (manufactured by Teraoka Co., Ltd.) throughout the cleansed arm. The cleansed arm was felt with the other hand (thoroughly prerinsed with tap water) to evaluate the absence of slimy feeling. This evaluation was carried out according to the following criteria, and the evaluation results were indicated by an average of scores given by 5 expert panelists:
5: no sliminess was felt.
4: sliminess was hardly felt.
3: sliminess was slightly felt.
2: sliminess was felt.
1: strong sliminess was felt.

TABLE 4

| | Component (mass %) | 34 | 35 | 36 | 37 | 38 | 39 | 40 | 41 | 42 | 43 | 44 |
|---|---|---|---|---|---|---|---|---|---|---|---|---|
| (A) | Copolymer 6 (DMAA/LMA = 6/4)Mw = 73,000 | 0.40 | 0.40 | 0.40 | 0.40 | 0.40 | 0.40 | | | | 0.40 | 0.40 |
| | Copolymer 11 (t-BuAA/LMA = 6/4)Mw = 81,000 | | | | | | | 0.40 | | | | |
| | Copolymer 12 (DMAA/LMA = 6/4)Mw = 16,000 | | | | | | | | 0.40 | | | |
| | Copolymer 18 (DMAA/LMA = 6/4)Mw = 480,000 | | | | | | | | | 0.40 | | |
| (b1) | Sodium polyoxyethylene(2) lauryl ether sulfate *2 | | | | | | | | | | | |
| | Ammonium polyoxyethylene(1) alkyl ether sulfate *3 | 5.00 | 2.50 | 1.50 | 3.50 | 1.00 | 2.00 | 2.00 | 2.00 | 2.00 | 2.00 | 2.00 |
| (b3) | Sodium polyoxyethylene(2.6) lauryl ether carboxylate *5 | | 2.50 | 3.50 | 1.50 | 4.00 | 3.00 | 3.00 | 3.00 | 3.00 | | |
| | Sodium polyoxyethylene(4.5) lauryl ether carboxylate *6 | | | | | | | | | | 3.00 | 3.00 |
| | Sodium salt of N-cocoyl-L-alanine *7 | | | | | | | | | | | |
| (C) | Water | balance | balance | balance | balance | balance | balance | balance | balance | balance | balance | balance |
| (E) | Alkyl (C10-16)polyglucoside *9 | | | | | | | | | | | 2.00 |
| | pH adjuster (malic acid) | q.s. | q.s. | q.s. | q.s. | q.s. | q.s. | q.s. | q.s. | q.s. | q.s. | q.s. |
| | Total | 100 | 100 | 100 | 100 | 100 | 100 | 100 | 100 | 100 | 100 | 100 |
| | (A)/(B) mass ratio | 0.080 | 0.080 | 0.080 | 0.080 | 0.080 | 0.080 | 0.080 | 0.080 | 0.080 | 0.080 | 0.080 |
| | (b1) + (b2) + (b3) total mass | 5.0 | 5.0 | 5.0 | 5.0 | 5.0 | 5.0 | 5.0 | 5.0 | 5.0 | 5.0 | 5.0 |
| | ((b1) + (b2))/(b3) mass ratio | — | 1.00 | 0.43 | 2.33 | 0.25 | 0.67 | 0.67 | 0.67 | 0.67 | 0.67 | 0.67 |
| | pH (20-fold dilution) | 6.9 | 7.0 | 7.5 | 6.9 | 6.9 | 7.0 | 7.0 | 7.0 | 7.0 | 7.0 | 7.0 |
| | Foaming quickness | 3.8 | 4.2 | 4 | 4.2 | 3.8 | 4.2 | 4.2 | 4.2 | 4.2 | 4.2 | 4.6 |
| | Foam quality upon cleansing | 4.2 | 4.6 | 4.8 | 4.4 | 4.6 | 4.6 | 4.4 | 4.4 | 4.6 | 4.4 | 4.4 |
| | Foam volume upon cleansing | 4.4 | 4.4 | 4.2 | 4.4 | 4.2 | 4.6 | 4.4 | 4.4 | 4.2 | 4.6 | 4.6 |
| | Feeling of foam thickness upon cleansing | 3.4 | 3.8 | 4 | 3.6 | 3.6 | 4 | 3.8 | 3.6 | 3.6 | 4 | 4 |
| | Absence of feeling of residues on skin at completion of rinsing | 4.6 | 4.8 | 4.8 | 4.2 | 4.6 | 4.8 | 4.8 | 4.6 | 4.6 | 4.8 | 4.8 |
| | Strength of stop feeling at completion of rinsing | 4.4 | 4.4 | 4.2 | 4 | 4.2 | 4.4 | 4.4 | 4.4 | 4.4 | 4.4 | 4.4 |
| | Skin feel immediately after towel-drying | 3 | 2.8 | 2.8 | 2.8 | 2.8 | 3 | 2.8 | 2.8 | 2.8 | 3 | 2.8 |
| | Skin feel after drying (natural bare skin feeling without feeling of residues on skin) | 8 | 8 | 7 | 8 | 8 | 8 | 8 | 8 | 7 | 8 | 9 |
| | Skin feel after drying (smooth and moist feeling of skin without powdery texture) | 8 | 7 | 8 | 7 | 8 | 9 | 8 | 8 | 8 | 9 | 9 |
| | Absence of sliminess at initial stage of rinsing | 3.2 | 4.4 | 4.4 | 4 | 4.6 | 4.6 | 4.6 | 4.6 | 4.4 | 4.4 | 4.4 |

TABLE 4-continued

| | Component (mass %) | Example 45 | 46 | 47 | 48 | 49 | 50 | 51 | 52 | 53 | 54 |
|---|---|---|---|---|---|---|---|---|---|---|---|
| (A) | Copolymer 6 (DMAA/LMA = 6/4)Mw = 73,000 | 0.40 | 0.40 | 0.40 | 0.40 | 0.40 | 0.40 | 0.40 | 0.40 | 0.40 | 1.00 |
| | Copolymer 11 (t-BuAA/LMA = 6/4)Mw = 81,000 | | | | | | | | | | |
| | Copolymer 12 (DMAA/LMA = 6/4)Mw = 16,000 | | | | | | | | | | |
| | Copolymer 18 (DMAA/LMA = 6/4)Mw = 480,000 | | | | | | | | | | |
| (b1) | Sodium polyoxyethylene(2) lauryl ether sulfate *2 | 5.00 | 2.00 | 2.00 | 2.00 | 2.50 | 2.50 | | | | |
| | Ammonium polyoxyethylene(1) alkyl ether sulfate *3 | | | | | | | 10.00 | 5.00 | 9.00 | 4.00 |
| (b3) | Sodium polyoxyethylene(2.6) lauryl ether carboxylate *5 | | 3.00 | 3.00 | | | | | 5.00 | 1.00 | 6.00 |
| | Sodium polyoxyethylene(4.5) lauryl ether carboxylate *6 | | | | | | | | | | |
| | Sodium salt of N-cocoyl-L-alanine *7 | | | | 3.00 | 2.50 | 2.50 | | | | |
| (C) | Water | balance | balance | balance | balance | balance | balance | balance | balance | balance | balance |
| (E) | Alkyl (C10-16)polyglucoside *9 | | | 2.00 | | | 2.00 | | | | |
| | pH adjuster (malic acid) | q.s. | q.s. | q.s. | q.s. | q.s. | q.s. | q.s. | q.s. | q.s. | q.s. |
| | Total | 100 | 100 | 100 | 100 | 100 | 100 | 100 | 100 | 100 | 100 |
| | (A)/(B) mass ratio | 0.080 | 0.080 | 0.080 | 0.080 | 0.080 | 0.080 | 0.040 | 0.040 | 0.040 | 0.100 |
| | (b1) + (b2) + (b3) total mass | 5.0 | 5.0 | 5.0 | 5.0 | 5.0 | 5.0 | 10.0 | 10.0 | 10.0 | 10.0 |
| | ((b1) + (b2))/(b3) mass ratio | — | 0.67 | 0.67 | 0.67 | 1.00 | 1.00 | — | 1.00 | 9.00 | 0.67 |
| | pH (20-fold dilution) | 6.9 | 6.9 | 7.0 | 7.5 | 7.5 | 7.5 | 6 | 6.5 | 7.0 | 7.0 |
| | Foaming quickness | 3.8 | 4 | 4.4 | 4.2 | 4.4 | 4.6 | 4 | 4.4 | 4.4 | 4.4 |
| | Foam quality upon cleansing | 4.2 | 4.2 | 4.2 | 4.4 | 4.4 | 4.4 | 4 | 4.8 | 4.2 | 4.6 |
| | Foam volume upon cleansing | 4.4 | 4.4 | 4.6 | 4.4 | 4.4 | 4.6 | 4.4 | 4.6 | 4.4 | 4.6 |
| | Feeling of foam thickness upon cleansing | 3.4 | 3.6 | 3.8 | 3.8 | 3.8 | 3.8 | 3 | 4 | 3.4 | 4 |
| | Absence of feeling of residues on skin at completion of rinsing | 4.8 | 4.8 | 4.8 | 4.8 | 4.8 | 4.8 | 4 | 4.8 | 4.6 | 4.6 |
| | Strength of stop feeling at completion of rinsing | 4.4 | 4.2 | 4.2 | 4.2 | 4.4 | 4.4 | 3.6 | 4.2 | 4 | 4.2 |
| | Skin feel immediately after towel-drying | 2.8 | 2.8 | 2.8 | 2.8 | 2.8 | 2.8 | 2.4 | 3 | 2.6 | 3 |
| | Skin feel after drying (natural bare skin feeling without feeling of residues on skin) | 9 | 9 | 9 | 8 | 9 | 9 | 7 | 8 | 8 | 9 |
| | Skin feel after drying (smooth and moist feeling of skin without powdery texture) | 8 | 8 | 8 | 8 | 8 | 8 | 7 | 8 | 8 | 8 |
| | Absence of sliminess at initial stage of rinsing | 3 | 4.2 | 4.2 | 4.4 | 4.4 | 4.4 | 3 | 4.2 | 3.6 | 4.6 |

*2 Active component of EMAL 125A manufactured by Kao Corp.
*3 Active component of EMAL 227 manufactured by Kao Corp.
*5 Active component of AKYPO LM-26SD manufactured by Kao Corp.
*6 Active component of KAO AKYPO RLM-45NV manufactured by Kao Corp.
*7 Active component of Amilite GCK-12B manufactured by Ajinomoto Co., Inc.
*9 Active component of AG-124 manufactured by Kao Corp.

Examples 55 to 72

In the same way as in Examples 1 to 33, each cleansing composition shown in Table 5 was produced and evaluated for foaming quickness, foam quality upon cleansing, foam volume upon cleansing, feeling of foam thickness upon cleansing, absence of feeling of residues on the skin at the completion of rinsing, strength of stop feeling at the completion of rinsing, skin feel immediately after towel-drying, and skin feel after drying (natural bare skin feeling without feeling of residues on the skin, and smooth and moist feeling of the skin without powdery texture). The results are also shown in Table 5.

TABLE 5

| Component (mass %) | Example 55 | 56 | 57 | 58 | 59 | 60 | 61 | 62 | 63 | 64 | 65 | 66 | 67 | 68 | 69 | 70 | 71 | 72 |
|---|---|---|---|---|---|---|---|---|---|---|---|---|---|---|---|---|---|---|
| (A) Copolymer 6 (DMAA/LMA = 6/4)Mw = 73,000 | 0.40 | 0.40 | 0.40 | 0.40 | 0.40 | 1.00 | 1.00 | 2.00 | 0.40 | 0.40 | 0.40 | | 0.40 | 0.40 | 0.40 | 0.40 | 0.40 | 0.40 |
| Copolymer 11 (t-BuAA/LMA = 6/4)Mw = 81,000 | | | | | | | | | | | | 0.40 | | | | | | |
| (B) Sodium polyoxyethylene(2) lauryl ether sulfate *2 | | | | | | | | | | | | | | | | | | |
| Ammonium polyoxyethylene(1) alkyl ether sulfate *3 | 10.00 | 10.00 | 10.00 | 10.00 | 10.00 | 10.00 | 10.00 | 10.00 | | | 5.00 | 10.00 | 10.00 | 10.00 | 5.00 | | | |
| Sodium polyoxyethylene(2,6) lauryl ether carboxylate *5 | | | | | | | | | 10.00 | 5.00 | | | | | 5.00 | | 10.00 | |
| Sodium salt of N-cocoyl-L-alanine *7 | | | | | | | | | | | | | | | | 10.00 | | 5.00 |
| (C) Water | balance | balance | balance | balance | balance | balance | balance | balance | balance | balance | balance | balance | balance | balance | balance | balance | balance | balance |
| (E) Alkyl (C10-16) polyglucoside *9 | | 0.05 | 0.20 | 0.50 | 1.00 | 0.20 | 0.50 | 0.10 | 0.20 | 0.20 | 0.20 | 0.20 | | 0.20 | 0.20 | 0.20 | 0.20 | 0.20 |
| (F) Potassium aluminum sulfate *13 | | | | | | | | | | | | | 0.20 | 3.00 | 3.00 | | | |
| Magnesium chloride *14 | | | | | | | | | | | | | | 0.20 | 0.20 | | | |
| pH adjuster (malic acid) | | | | | | | | | | q.s. | | | | | | | | |
| pH adjuster (NaOH) | q.s. | q.s. | q.s. | q.s. | q.s. | q.s. | q.s. | q.s. | q.s. | | q.s. | q.s. | q.s. | q.s. | q.s. | q.s. | q.s. | q.s. |
| Total | 100 | 100 | 100 | 100 | 100 | 100 | 100 | 100 | 100 | 100 | 100 | 100 | 100 | 100 | 100 | 100 | 100 | 100 |
| (A)/(B) mass ratio | 0.040 | 0.040 | 0.040 | 0.040 | 0.040 | 0.100 | 0.100 | 0.200 | 0.040 | 0.040 | 0.080 | 0.040 | 0.040 | 0.040 | 0.040 | 0.040 | 0.040 | 0.080 |
| (A)/(F) | — | 8.00 | 2.00 | 0.80 | 0.40 | 5.00 | 2.00 | 20.00 | 2.00 | 2.00 | 2.00 | 2.00 | 2.00 | 2.00 | 2.00 | 2.00 | 2.00 | 2.00 |
| (B)/(F) | — | 200.0 | 50.0 | 20.0 | 10.0 | 50.0 | 20.0 | 100.0 | 50.0 | 50.0 | 25.0 | 50.0 | 50.0 | 50.0 | 50.0 | 50.0 | 50.0 | 25.0 |
| pH (20-fold dilution) | 6.0 | 5.6 | 5.8 | 6.0 | 7.0 | 6.0 | 6.9 | 6.0 | 6.5 | 6.5 | 6.0 | 6.0 | 6.0 | 6.5 | 6.5 | 7.0 | 6.0 | 6.0 |
| Foaming quickness | 4 | 4 | 4 | 3.8 | 3.8 | 4.2 | 4 | 3.8 | 3.8 | 4.2 | 3.8 | 4 | 4 | 4.4 | 4.4 | 3.8 | 4.2 | 3.8 |
| Foam quality upon cleansing | 4 | 4.2 | 4.2 | 4.2 | 4 | 4.4 | 4.4 | 4.8 | 4.6 | 4.6 | 4.2 | 4.2 | 4.2 | 4.2 | 4.6 | 4.6 | 4.6 | 4.2 |
| Foam volume upon cleansing | 4.4 | 4.4 | 4.4 | 4.2 | 4 | 4.4 | 4 | 4.4 | 4 | 4.2 | 4.4 | 4.4 | 4.4 | 4.6 | 4.6 | 4 | 4.6 | 4.4 |
| Feeling of foam thickness upon cleansing | 3 | 3.2 | 3.2 | 3.2 | 3 | 3.6 | 3.4 | 3.6 | 3.6 | 3.6 | 3.2 | 3 | 3 | 3.4 | 3.6 | 3.6 | 3.4 | 3.2 |
| Absence of feeling of residues on skin at completion of rinsing | 4 | 4.6 | 4.6 | 4.4 | 4 | 4.6 | 4.6 | 4.2 | 4.6 | 4.6 | 4.8 | 4.6 | 4.6 | 4.6 | 4.6 | 4.4 | 4.6 | 4.8 |
| Strength of stop feeling at completion of rinsing | 3.6 | 4 | 4.4 | 4.4 | 4.6 | 4.6 | 4.6 | 4.2 | 4.6 | 4.6 | 4.6 | 4.4 | 4.6 | 4.6 | 4.6 | 4.4 | 4.6 | 4.4 |

TABLE 5-continued

| Component (mass %) | Example | | | | | | | | | | | | | | | | | |
|---|---|---|---|---|---|---|---|---|---|---|---|---|---|---|---|---|---|---|
| | 55 | 56 | 57 | 58 | 59 | 60 | 61 | 62 | 63 | 64 | 65 | 66 | 67 | 68 | 69 | 70 | 71 | 72 |
| Skin feel immediately after towel-drying | 2.4 | 2.6 | 2.6 | 2.8 | 2.4 | 2.6 | 2.4 | 2.6 | 2.8 | 2.8 | 2.8 | 2.6 | 2.8 | 2.6 | 2.8 | 2.6 | 2.8 | 2.8 |
| Skin feel after drying (natural bare skin feeling without feeling of residues on skin) | 7 | 8 | 8 | 8 | 6 | 7 | 8 | 6 | 9 | 9 | 7 | 8 | 8 | 8 | 9 | 8 | 8 | 8 |
| Skin feel after drying (smooth and moist feeling of skin without powdery texture) | 7 | 8 | 8 | 7 | 7 | 8 | 8 | 7 | 8 | 8 | 8 | 8 | 8 | 8 | 8 | 8 | 8 | 8 |

*2 Active component of EMAL 125A manufactured by Kao Corp.
*3 Active component of EMAL 227 manufactured by Kao Corp.
*5 Active component of AKYPO LM-26SD manufactured by Kao Corp.
*7 Active component of Amilite GCK-12B manufactured by Ajinomoto Co., Inc.
*9 Active component of AG-124 manufactured by Kao Corp.
*13 Active component of burnt alum manufactured by Taimei Chemicals Co., Ltd.
*14 Active component of magnesium chloride manufactured by Wako Pure Chemical Industries, Ltd.

Each cleansing composition below was prepared according to a routine method. All of the obtained cleansing compositions foam quickly upon cleansing, are excellent in foam quality with a sufficient foam volume, and are free from feeling of residues on the skin at the completion of rinsing, and offer favorable stop feeling. In addition, these cleansing compositions were judged to be able to produce a non-sticky dry feel because of few residues on the skin immediately after towel-drying following cleansing, and to produce natural bare skin feeling without feeling of residues on the skin after drying.

Example 73 (Cleansing Composition)

(Composition)

| Copolymer 6 (DMAA/LMA = 6/4; Mw = 73,000) 0.4 (% by mass) | |
|---|---|
| Sodium polyoxyethylene(2) lauryl ether sulfate*1 | 7.0 |
| Lauryl hydroxy sulfobetaine*8 | 3.5 |
| Alkyl (C10-16) polyglycoside*9 | 2.0 |
| Propylene glycol*15 | 4.0 |
| Fragrance | 1.0 |
| Sodium benzoate*16 | 0.5 |
| Glycol distearate*17 | 3.0 |
| Citric acid | q.s. |
| Water | balance |
| Total | 100 |
| (pH 7) | |

Example 74 (Cleansing Composition)

| Copolymer 6 (DMAA/LMA = 6/4; Mw = 73,000) 0.3 (% by mass) | |
|---|---|
| Sodium polyoxyethylene(2) lauryl ether sulfate*1 | 12.0 |
| Polyglyceryl monolaurate*18 | 1.0 |
| Propylene glycol*15 | 5.0 |
| Glycerin*19 | 5.0 |
| Fragrance | 0.1 |
| Sodium benzoate*16 | 0.5 |
| Disodium ethylenediaminetetraacetic acid*20 | 0.2 |
| Isopropylmethylphenol*21 | 0.2 |
| Citric acid | q.s. |
| Water | balance |
| Total | 100 |
| (pH 5) | |

Example 75 (Cleansing Composition)

| Copolymer 11 (t-BuAA/LMA = 6/4; Mw = 81,000) 0.5 (% by mass) | |
|---|---|
| Sodium polyoxyethylene(2) lauryl ether sulfate*1 | 6.0 |
| Sodium polyoxyethylene(4.5)lauryl ether carboxylate*6 | 3.0 |
| Sodium salt of N-cocoyl-L-alanine*7 | 3.0 |
| Lauryl hydroxy sulfobetaine*8 | 3.0 |
| Isostearyl glyceryl ether*22 | 0.5 |
| Propylene glycol*15 | 4.0 |
| Fragrance | 1.0 |
| Phenoxyethanol*23 | 0.5 |
| Glycol disterate*17 | 2.0 |
| Malic acid | q.s. |
| Water | balance |
| Total | 100 |
| (pH 8.5) | |

Example 76 (Cleansing Composition)

| Copolymer 6 (DMAA/LMA = 6/4; Mw = 73,000) 0.4 (% by mass) | |
|---|---|
| Sodium polyoxyethylene(2) lauryl ether sulfate*1 | 5.0 |
| Sodium polyoxyethylene(2.6)lauryl ether carboxylate*3 | 4.0 |
| Lauric acid*24 | 0.5 |
| Lauryl hydroxy sulfobetaine*8 | 3.5 |
| Alkyl (C10-16) polyglycoside*9 | 4.0 |
| Propylene glycol *15 | 3.0 |
| Fragrance | 0.5 |
| Sodium benzoate*16 | 0.5 |
| Malic acid | q.s. |
| Water | balance |
| Total | 100 |
| (pH 7) | |

*15: Active component of propylene glycol manufactured by Asahi Glass Co., Ltd.

*16: Active component of sodium benzoate manufactured by Aioi ChemiScience Co., Ltd.

*17: Active component of EMANON 3201M-V manufactured by Kao Corp.

*18: Active component of Sunsoft M-12J manufactured by Taiyo Kagaku Co., Ltd.

*19: Active component of cosmetic concentrated glycerin manufactured by Kao Corp.

*20: Active component of Clewat N manufactured by Nagase ChemteX Corporation

*21: Active component of isopropylmethylphenol manufactured by Osaka Kasei Co., Ltd.

*22: Active component of PENETOL GE-IS manufactured by Kao Corp.

*23: Active component of High-Solve EPH manufactured by Toho Chemical Industry Co., Ltd.

*24: Active component of LUNAC L-98 manufactured by Kao Corp.

The invention claimed is:

1. A cleansing composition comprising components (A), (B), and (C):
(A) from 0.02% by mass to 10% by mass of a polymer comprising 85 to 100% by mass of a1 and a2 as constitutional units:
a1: a constitutional unit represented by formula (1):

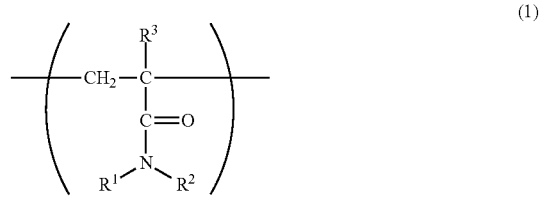

wherein $R^1$ and $R^2$ are the same or different and each represents an alkyl group having 1 to 4 carbon atoms and optionally having a hydroxy group, or a hydrogen atom, and $R^3$ represents a hydrogen atom or a methyl group, and a2: a constitutional unit represented by formula (2):

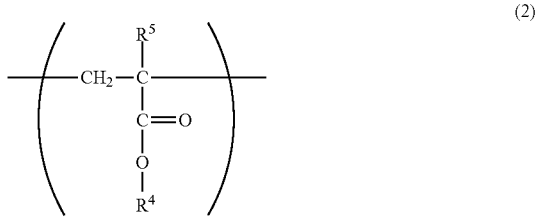

wherein $R^4$ represents a linear or branched alkyl group having 1 to 22 carbon atoms, and $R^5$ represents a hydrogen atom or a methyl group;

(B) from 0.5% by mass to 40% by mass of an anionic surfactant comprising: i) at least one of a compound b1 represented by formula (3) and a compound b2 represented by formula (4); and ii) a compound b3 represented by formula (5):

b1: formula (3):

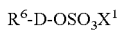
$$R^6\text{-D-OSO}_3X^1 \quad (3)$$

wherein $R^6$ represents a linear or branched alkyl group or alkenyl group having 10 to 22 carbon atoms, D represents $-(OCH_2CH_2)_n-$, in which n represents a number of 0 to 10, and $X^1$ represents an alkali metal, an alkaline earth metal, an ammonium, or an organic base, b2: formula (4):

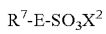
$$R^7\text{-E-SO}_3X^2 \quad (4)$$

wherein $R^7$ represents an optionally substituted linear or branched alkyl group or alkenyl group having 10 to 22 carbon atoms, E represents $-(OCH_2CH_2)_m-$ or $-CO-O-C_2H_4-$, in which m represents a number of 0 to 10, and $X^2$ represents an alkali metal, an alkaline earth metal, an ammonium, or an organic base, and b3: formula (5):

$$R^8\text{-G-COOX}^3 \quad (5)$$

wherein $R^8$ represents a linear or branched alkyl group or alkenyl group having 10 to 22 carbon atoms, G represents $-(OCH_2CH_2)_p-OCH_2-$ or $-CO-NH-CR^9H-$, in which p represents a number of 0 to 10, and $R^9$ represents a hydrogen atom or a methyl group, and $X^3$ represents an alkali metal, an alkaline earth metal, an ammonium, or an organic base; and (C) water, wherein a mass ratio between the sum of b1 and b2, and b3, ((b1+b2)/(b3)), is from 0.1 to 9.

2. The cleansing composition according to claim 1, wherein component (A) has a weight-average molecular weight of 10,000 to 500,000.

3. The cleansing composition according to claim 1, wherein component (A) has a weight-average molecular weight of 50,000 to 100,000.

4. The cleansing composition according to claim 1, wherein a mass ratio between a1 and a2, a1/a2 in the component (A) is from 5/95 to 95/5.

5. The cleansing composition according to claim 1, wherein a mass ratio between a1 and a2, a1/a2, in the component (A) is from 20/80 to 80/20.

6. The cleansing composition according to claim 1, wherein a1 in component (A) is derived from a monomer selected from the group consisting of N,N-dimethylacrylamide, N,N-diethylacrylamide, N-2-hydroxyethylacrylamide, and N-t-butylacrylamide.

7. The cleansing composition according to claim 1, wherein a2 in component (A) is represented by formula (2) wherein $R^4$ is a linear or branched alkyl group having 4 to 18 carbon atoms.

8. The cleansing composition according to claim 1, wherein component (B) is at least one member selected from the group consisting of:
   b1: alkyl sulfate having a linear or branched alkyl group having 10 to 22 carbon atoms and alkyl ether sulfate having a linear or branched alkyl group having 10 to 22 carbon atoms;
   b2: sulfonate having a linear or branched alkyl group having 10 to 22 carbon atoms, alkenyl sulfonate having a linear or branched alkenyl group having 10 to 22 carbon atoms, linear or branched fatty acid ester sulfonate having 10 to 22 carbon atoms, dialkyl sulfosuccinate having a linear or branched alkyl group having 10 to 22 carbon atoms, and alkyloyl taurate having taurine bonded to a linear or branched fatty acid having 10 to 22 carbon atoms; and
   b3: alkyl ether carboxylate having a linear or branched alkyl group having 10 to 22 carbon atoms and linear or branched fatty acid acyl amino acid salt having 10 to 22 carbon atoms.

9. The cleansing composition according to claim 1, wherein a mass ratio between component (A) and component (B), (A)/(B) is from 0.0025 to 8.

10. The cleansing composition according to claim 1, wherein a mass ratio between component (A) and component (B), (A)/(B), is from 0.007 to 1.

11. The cleansing composition according to claim 1, wherein a mass ratio between component (A) and component (B), (A)/(B) is from 0.035 to 0.2.

12. The cleansing composition according to claim 1, further comprising (E) a nonionic surfactant having HLB of 11 or higher.

13. A method of cleaning skin, comprising:
   contacting skin with a cleansing composition according to claim 1; and thereafter
   rinsing the cleansing composition from the skin.

* * * * *